US008867039B2

(12) United States Patent
Ruggiero et al.

(10) Patent No.: US 8,867,039 B2
(45) Date of Patent: Oct. 21, 2014

(54) METHODS AND APPARATUS TO OBTAIN SUSPENDED PARTICLE INFORMATION

(71) Applicants: Steven Ruggiero, Niles, MI (US); Carol Tanner, Niles, MI (US)

(72) Inventors: Steven Ruggiero, Niles, MI (US); Carol Tanner, Niles, MI (US)

(73) Assignee: University of Notre Dame du Lac, Notre Dam, IN (US)

( * ) Notice: Subject to any disclaimer, the term of this patent is extended or adjusted under 35 U.S.C. 154(b) by 0 days.

(21) Appl. No.: 13/908,637

(22) Filed: Jun. 3, 2013

(65) Prior Publication Data

US 2014/0022545 A1   Jan. 23, 2014

Related U.S. Application Data

(63) Continuation of application No. 13/125,613, filed as application No. PCT/US2009/061853 on Oct. 23, 2009, now Pat. No. 8,456,635.

(60) Provisional application No. 61/197,192, filed on Oct. 24, 2008, provisional application No. 61/211,141, filed on Mar. 26, 2009.

(51) Int. Cl.
| | | |
|---|---|---|
| *G01N 21/00* | (2006.01) | |
| *G01N 15/02* | (2006.01) | |
| *G01N 21/51* | (2006.01) | |
| G01N 21/47 | (2006.01) | |
| G02B 21/00 | (2006.01) | |
| G02B 21/18 | (2006.01) | |

(52) U.S. Cl.
CPC ............ *G01N 21/00* (2013.01); *G01N 15/0205* (2013.01); *G01N 21/51* (2013.01); *G01N 2021/4707* (2013.01); *G01N 2015/0294* (2013.01); *G02B 21/0096* (2013.01); *G02B 21/18* (2013.01)
USPC ............................ 356/436; 356/440; 356/441

(58) Field of Classification Search
CPC .................................................. G01N 21/8507
USPC .................................................. 356/432–442
See application file for complete search history.

(56) References Cited

U.S. PATENT DOCUMENTS

2007/0211251 A1* 9/2007 Weischselbaum ............ 356/338

OTHER PUBLICATIONS

International Preliminary Report on Patentability and Written Opinion of the International Searching Authority of PCT/US2012/54818, date of issuance Mar. 12, 2014, 9 pgs.

* cited by examiner

*Primary Examiner* — Michael P Stafira
(74) *Attorney, Agent, or Firm* — Greenberg Traurig, LLP

(57) ABSTRACT

Example methods and apparatus for obtaining suspended particle information are disclosed. A disclosed example method includes emitting light from a light source, dividing the light source into a first path and a second path, and directing the first path to a first container comprising a plurality of particles in a suspension material. The example method also includes directing the second path to a second container containing a suspension material devoid of particles, retrieving a first transmission value of the first path through the first container, and retrieving a second transmission value of the second path through the second container. The example method further includes directing the first and second paths to the second and first containers, respectively, retrieving a third transmission value of the first path a through the second container, retrieving a fourth transmission value of the second path through the first container, and calculating a ratio of the first and second transmission values to the third and fourth transmission values to determine an indication of transmissivity for a given wavelength.

18 Claims, 13 Drawing Sheets

METHODS AND APPARATUS TO OBTAIN SUSPENDED PARTICLE INFORMATION

RELATED APPLICATION

This application is a continuation of U.S. patent application Ser. No. 13/125,613, now U.S. Pat. No. 8,456,635, filed Jun. 28, 2011, entitled "Methods and Apparatus to Obtain Suspended Particle Information," which claims the benefit of U.S. Provisional Patent Application No. 61/197,192, entitled "Scanning Laser Assaying System," filed on Oct. 24, 2008, and U.S. Provisional Patent Application No. 61/211,141, entitled "Scanning Laser Assaying System," filed on Mar. 26, 2009, each of which are hereby incorporated by reference in their entireties.

TECHNICAL FIELD

The present disclosure relates to transmission based particle measurement, and in particular, to methods and apparatus to obtain suspended particle information.

BACKGROUND

Identifying a number of objects suspended in a medium is typically accomplished via particle counters employing a microscope to acquire an image of a section from the medium. Assuming that the particles remain in a homogeneous suspended state, a counted total of each of the objects within the section may be used to project a value representative of the density of objects in the medium. Automated particle sizing and counting on a microscopic scale began around 1954 with a Coulter Counter, which employed electrical sensing zone techniques. In particular, the particles to be measured were dispersed in an electrolyte solution and passed through a tube having a narrow aperture with electrodes on either side. The narrow aperture restricts the particles so that only a single particle passes through at one time through an electric field. As the particles pass through the aperture, a resistance is measured, which is related to a corresponding particle size.

Techniques developed after the Coulter Counter evolved to reduce the time required to measure particles and the efficiency at which particles were measured via diffraction and/or scattering techniques using light sources, such as single wavelength lasers. Generally speaking, diffraction techniques identify characteristic signatures of light after a particle influences the incident light. Such characteristic signatures may be derived from ring-shaped intensity patterns indicative of particle size, in which closely situated rings identify corresponding particles having a relatively larger size and widely situated rings identify corresponding particles having a relatively smaller size. The diffraction techniques permitted, an improved ability to measure particles having smaller sizes than were capable via the Coulter Counter. Diffraction measurements allowed measurements down to particles having a 20 nano-meter (nm) diameter, but do not collect all of the scattered light, thereby limiting the resolution and sensitivity. Scattering techniques typically use a single detector, multiple detectors or an array of detectors, but only collect a fraction of the scattered light, which limit resulting resolution and/or sensitivity.

Scattering techniques to determine a size and/or distribution of particles include laser diffraction, dynamic light scattering, angle dependent scattering, in which a fixed-wavelength laser is directed on a solution of particles and a single detector, multiple detectors or an array of detectors is arranged to collect light scattered from the solution. The techniques that analyze scattered light include dynamic light scattering, angular dependent scattering, laser diffraction, and photon cross correlation spectroscopy. Such techniques employ a single detector, multiple detectors, or an array of detectors and may provide information indicative of the strength and distribution of the light to derive particle size and/or distribution information. Accordingly, the diffraction/light scattering techniques miss a substantial fraction of the total possible paths of flight that are scattered by one or more particles in the sample.

DETAILED DESCRIPTION

Figure 1A:
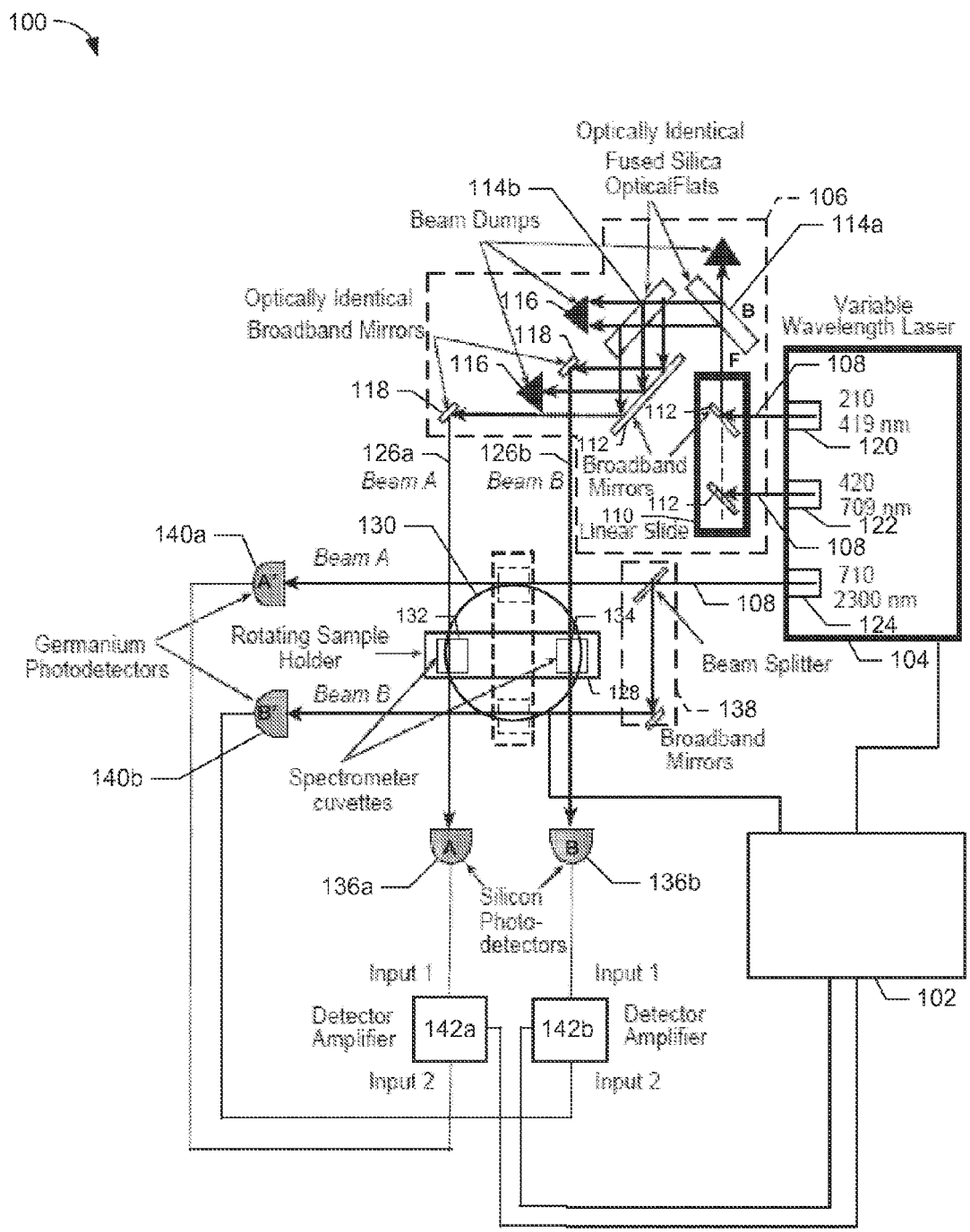
FIGS. 1A, 1B and 1C are example transmission-based particle measurement systems to acquire suspended particle information.

Identifying particle sizes of materials suspended in a solution (e.g., in sprays, powders, suspensions, etc.) have several applications in various industries. For example, some hydraulic equipment requires that fluids and/or oils used under pressure conform to quality standards related to foreign particle sizes and/or a density of foreign particles. In the event that such fluids and/or oils exceed a foreign particle density threshold and/or a foreign particle size threshold, damage to the hydraulic equipment may occur and/or result potentially harmful safety concerns for equipment operators.

Additionally, industrial applications for determining particle sizes and/or particle densities in solution include de-ionized water and acid quality control for semiconductor manufacturing, and/or silt and sediment analysis. Further, industrial applications may include, without limitation, biological particle studies, studies of oceanographic saline samples, chemical abrasive quality control and specification, biological cellular analysis, virus analysis and/or virus identification. Suspension media may include liquid, gas or vacuum. Particle types may include, but are not limited to atoms, molecules, metals, oxides, semiconductors and/or chemical compounds. Generally speaking, particle sizing and counting techniques are of particular interest in the fields of biology (e.g., biological weaponry identification), pharmaceuticals and/or medicinal instrumentation. Particle size detection by one or more scattering-based techniques are typical methods employed by industry research personnel because of its robust implementation, ability to size various types of particles, and availability of off-the-shelf hardware. However, scattering-based techniques exhibit one or more limitations related to instrumentation sensitivity and particle size resolution based on, for example, the particle composition (e.g., metallic particles, plastic particles, biological particles, etc.). Additionally, scattering-based techniques exhibit limitations related to measuring particle sizes in circumstances where a solution may have a quantity of different sized particles.

The methods and apparatus described herein employ particle size measurements, particle distribution measurements, absolute particle number measurements, and absolute particle density measurements via light transmission rather than scattering-based techniques. As a result, particle sizes may be measured down to 10 nm or less, and up to 3000 nm or more, in which the range is a function of in part, the light source(s), detector(s), and/or other components employed. Nonetheless, the ability to measure particle sizes as small as 10 nm possibilities for the study of a wider variety of biological systems, such as viruses and proteins that scattering-based techniques fail to accomplish. Additionally, while the scattering-based techniques identify an estimated particle distribution based on a probability, the methods and apparatus described herein identify absolute particle number (e.g., total particle count) rather than the relative amount of each particle type. The methods and apparatus described herein also improve upon particle identification by providing information related to a particle major axis and a minor axis. As a result, blood analysis using the methods and apparatus described herein provide biological particle size, shape and/or count information, including the ability to identify the presence of bacteria, viruses, proteins and/or other particles and cells.

In the illustrated example of FIG. 1A, a transmission-based particle measurement system 100 includes a transmission measurement controller 102, a variable wavelength laser 104 and a first mirror array 106 to beam split and/or direct source laser light 108 from the example variable wavelength laser 104. The example first mirror array 106 includes a linear slide 110, broadband mirrors 112, and optically identical fused silica optical flats 114a, 114b to, in part, facilitate beam splitting. The example mirror array 106 also includes beam dumps 116 and optically identical broadband mirrors 118. In operation, the source laser light 108 may be emitted from the variable wavelength laser 104 from any number of ports, such as a first wavelength port 120, a second wavelength port 122 and a third wavelength port 124. The example first wavelength port 120 emits source laser light having a wavelength between 210 nm and 419 nm, the example second wavelength port 122 emits source laser light 108 having a wavelength between 420 nm and 709 nm, and the example third wavelength port 124 emits source laser light 108 having a wavelength between 710 nm and 2300 nm. Although the example variable wavelength laser source 104 include three example ports 120, 122, 124, any other type of variable wavelength light source (e.g., laser source, broadband light source, etc.) may be employed having greater or fewer output ports. For example, a laser source may employ a single port capable of outputting a frequency between 210 nm and 2300 nm, and/or any other wavelength range. The laser source may be the NT 342/UV by Ekspla Optics, which facilitates a laser pulse width of 4 ns and a repetition rate of 10 Hz. Additionally, the NT 342/UV employs a pump beam to achieve wavelengths between 1064 nm and 2300 nm.

The linear slide 110 is controlled by the example transmission measurement controller 102 to select light from one or more ports 120, 122, 124 and the broadband mirrors 112 on the slide 110 directs the laser light 108 to the optically identical fused silica optical flats 114a, 114b to create two optically, identical laser beams 126a (Beam A) and 126h (Beam B). A collimator (not shown) may be used to fix the beam radius at 1 millimeter (mm) prior to splitting the beam into two identical paths. The optically identical fused silica optical flats 114a, 114b may operate as beamsplitters, in which the first flat 114a may be placed at a 45° angle of incidence and produce two 90° partial reflections, one at a front surface (F) and one at a back surface (B) of the first flat 114a, and two 90° partial reflections, one at a back surface (B) and one at the front surface (F) of the example second flat 114b. The two beams A 126a and B 126b are then directed, via the optically identical broadband mirrors 118, toward a rotating sample holder 128 affixed to motor-controlled rotating platform 130. Residual light is absorbed in optical beam dumps 116. Beam A 126a and Beam B 126b have substantially identical intensities, but are spatially separated to reach corresponding spectrometer containers. Alternatively, Beam A 126a and Beam B 126b may be generated by two separate light sources (e.g., two laser sources) and fumed to exhibit optical beam characteristics as similar as possible.

The example rotating sample holder 128 holds spectrometer containers (cuvettes) for sample A 132 and sample B 134, which may be implemented as quartz containers that hold de-ionized water or the material to be analyzed. To eliminate errors and achieve improved performance results over scattering-based techniques (e.g., dynamic light scattering and/or diffraction techniques), balance measuring techniques are applied to a sample under test and a control sample. Errors may be introduced by, for example, apparatus variation, differences in detector characteristics, amplifier characteristics, sample container properties, laser light power fluctuation(s), transient vibration(s) and/or atmospheric variation(s). The balance measuring techniques include scanning the sample under test with a first laser beam and scanning the control sample with a second laser beam derived from the same laser. While the first and second laser beams, discussed in further detail below, are configured by the example measurement system 100 to exhibit beams having equal power, dimensions and/or polarization over all wavelengths, some variation and/or uncertainty may arise in each laser beam, each detector and/or any other environmental condition in which the example measurement system 100 operates. The balance measuring techniques include interchanging the sample under test and the control sample positions so that the first laser beam strikes the control sample and the second laser beam strikes the sample under test. As a result, the balance measuring techniques eliminate potential uncertainty due to variation of the example laser source 104, the mirror arrays 106, 138, Beam A 126a, Beam B 126b, containers for sample A 132 and sample B 134 and/or one or more detectors, such as an example first photodetector 136a and an example second photodetector 136b.

Balance measuring techniques may also include applying one or more filters to the source laser light 108 before it is split by optical flats 114a, 114b, thereby maintaining similar signal sizes of the laser light 108 across all wavelengths of interest. The one or more filters also minimize nonlinearities that may be associated with gains and/or efficiency characteristics of the example first and second photodetectors 136a, 136b. Other detector characteristics addressed by balance measurement techniques include matching the photodetectors so that their gains, efficiencies and/or response times are similar and/or independent of incident laser power from Beam A 126a and/or Beam B 126b. Additionally, the balance measuring techniques may include selecting two containers for sample A 132 and sample B 134 to be as similar as possible so that transmission difference between Beam A 126a and Beam B 126b are minimized. Balance measuring techniques may also include swapping the containers for sample A 132 and sample B 134 to account for differences in the transmission of the two containers.

Switching of the example spectrometer containers 132, 134 during the balance measurement techniques may occur by rotating the example motor controlled rotating platform 130 by 180 degrees. Without limitation, one or more broadband mirrors may be employed to switch Beam A 126a and Beam B 1261 to strike either of the example sample A 132 or sample B 134 to allow each sample to remain snot unless. Measurements are made by the first photo detector 136a that corresponds to Beam A 126a and the second photodetector 136b that corresponds to Beam B 126b. In the event that one or more alternate photodetectors are employed to accommodate one or more alternate ranges of laser wavelength (e.g., to better match ideal photodetector sensitivity operating range(s)), a second mirror array 138 may be employed to direct laser light output toward a third detector 140a and a fourth detector 140b. For example, the first and second photodetectors 136a, 136b may be silicon photodetectors that are ideally suited and/or responsive to laser wavelengths between 210 nm and 709 nm, but experience diminished sensitivity for laser wavelengths at or above 710 nm. On the other hand, the third and fourth photodetectors 140a, 140b may be Germanium photodetectors that are, ideally suited and/or responsive to laser wavelengths between 710 nm and 2300 nm, but experience diminished sensitivity for laser wavelengths at or below 709 nm. For example, Germanium detectors are typically used for wavelengths between 710 nm and 2300 nm due to their superior efficiency as compared to Silicon detectors in such wavelength ranges.

While the illustrated example transmission-based particle measurement system 100 includes four example photodetectors 136a, 136b, 140a, 140b, any number of photodetectors may be employed to accommodate one or more specific laser light wavelength(s) of interest. Each photodetector is communicatively connected to a first detector/amplifier 142a and a second detector/amplifier 142b, which are further communicatively connected in the example transmission measurement controller 102. Unlike scattering-based measurement techniques, the example transmission-based particle measurement system 100 employs a single detector for each incident laser light path to measure a resulting transmission power, thereby eliminating any need for an array of detectors in an effort to capture light scattering for angles other than zero ($\theta \neq 0$), as opposed to a zero angle of incidence ($\theta = 0$), which represents transmitted light.

For each selected wavelength ($\lambda$), the power for Beam A 126a and Beam B 126b have similar power values $P_A$ and $P_B$, respectively, and also have similar polarization values. Initially, Beam A 126a strikes the example sample A 132 containing the particle sample under study and Beam B 126b strikes the example sample B 134 containing a control suspension fluid (e.g., de-ionized water). At least one benefit realized by the balance measuring techniques when substantially simultaneously measuring transmission through both containers 132, 134 is that any laser power fluctuations from one laser pulse to the next laser pulse can be divided-out during one or more ratio computations, as described in further detail below. Corresponding photodetectors 142a, 142b receive transmitted light after passing through each sample 132, 134 to produce signals $D_{AP}(\lambda)$ and $D_{BP}(\lambda)$, respectively. $D_{AP}(\lambda)$ represents the signal from the first detector 142a from Beam A 126a through the particle sample with a suspension material (e.g., a suspension fluid, a gas, etc.) at wavelength ($\lambda$), and $D_{BF}(\lambda)$ represents the signal from the second detector 142b from Beam B 126b through the suspension fluid at wavelength ($\lambda$). The source wavelength ($\lambda$) is changed by a step value (e.g., 1 nm) and another measurement of the transmitted power through the particle sample and the suspension fluid is obtained as $D_{AP}(\lambda+\Delta)$ and $D_{BF}(\lambda+\Delta)$. The process of setting the laser wavelength, taking a measurement in each path, and changing the laser wavelength by a step value occurs for any number of iterations based on the starting wavelength ($\lambda_{START}$), the ending wavelength ($\lambda_{FINISH}$) and the wavelength step size.

As described above, to eliminate errors, the example transmission-based measurement system 100 employs balance measuring techniques that switch the location of example sample A 132 and sample B 134 via a 180 degree rotation after a first series of scanned laser wavelengths (a first sweep). As a result, instead of Beam A 126a striking example sample A 132, Beam A 126a now strikes example sample B 134 during a second series of scanned laser wavelengths (a second sweep). Similarly, instead of Beam B 126b striking example sample B 134, Beam B 126b now strikes example sample A 132 during the second sweep. Performing such balancing measuring techniques results in one or more benefits to the data calculated by the example transmission measurement controller 102. For example, the balancing measurement techniques allow the example transmission measurement controller 102 to calculate an absolute number of objects present in the sample under test rather than an estimate of the number and/or relative number of objects in the sample (which is indicative of results obtained when employing dynamic light scattering techniques). Additionally, the improved accuracy afforded by the balance measuring techniques allow the transmission measurement controller 102 to calculate a major axis and a minor axis for non-spherical detected particles. In other words, by, in part, scanning each container during a first sweep with Beam A 126a and Beam B 126b and then repeating the scan during a second sweep with each beam striking the opposite container, a corresponding dynamic range and sensitivity of the example transmission measurement controller 102 is improved over that of scattering-based techniques.

Balance measuring techniques may address one or more sources of potential error of the example transmission-based measurement system 100 of FIG. 1A. For example, in the event of light source variation (e.g., power fluctuation) from the example laser source 104 (or a broadband hot source, as described below in connection with FIGS. 1B and 1C), the example balance measuring techniques can nullify and/or minimize the effects of such variation on resulting particle measurement data. Further, because a single laser source is employed in the example transmission-based measurement system 100, any time-based power fluctuation(s) (and/or oilier variation(s)) may be detected substantially simultaneously at each detector to permit variation cancellation via the example balance measuring techniques (e.g., ratio cancellation). Other factors that may contribute to improved results in connection with balance measuring techniques include, but are not limited to, ensuring characteristic consistency between Beam A 126a and Beam B 126b. Characteristic consistency includes ensuring that Beam A 126a has a substantially identical path length as Beam B 126b, ensuring that Beam A 126a has a substantially identical attenuation characteristic(s) as Beam B 126b, ensuring that Beam A 126a has a substantially identical power characteristic as Beam B 126b and/or ensuring that Beam A 126a and Beam B 126b) have substantially identical polarization characteristics.

Figure 1B:
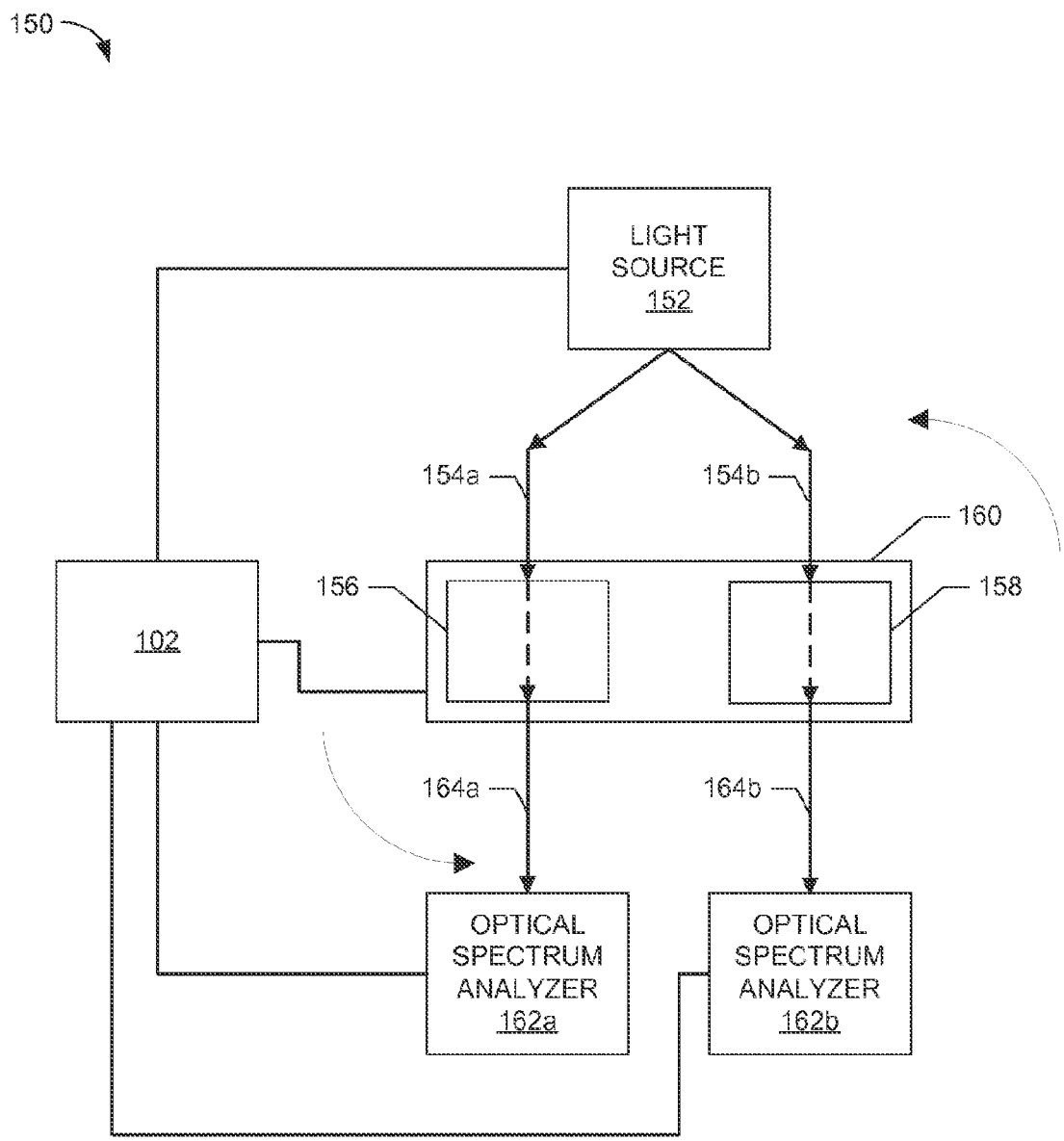

FIG. 1B illustrates another example transmission-based particle measurement system 150. In the illustrated example of FIG. 1B, as broadband light source 152 provides an incident light beam 154a, 154b directed at a sample under test 156 and a control sample 158, respectively. Each incident light beam 154a, 154b may be implemented in any manner such as, but not limited to, an optical array(s) and/or fiber optic splitter(s). The example sample under test 156 may include a container, crucible and/or other optically transmissive container that holds particles to be measured and/or that holds the control sample, as described above. Similarly, the control sample 158 may hold the suspension fluid, and both the sample under test 156 and control sample 158 may be interchanged by, for example, rotating the sample holder 160 by 180 degrees. Rotation of the example holder 160 may occur after an example optical spectrometer (OS) and/or spectrum analyzer 162a scans a transmitted beam 164a for one or more wavelengths of interest (e.g., a sweep of wavelengths of interest), and an example OS (and/or spectrum analyzer) 162b scans a transmitted beam 164b substantially simultaneously at one or more wavelengths of interest. The example transmission-based particle measurement system 150 of FIG. 1B employs the same measurement principles described herein, but uses the broadband light source for any number of desired wavelengths (e.g., infrared ranges, ultraviolet ranges, etc.) rather than the tunable laser 104 described in connection with FIG. 1A, and may allow particle measurement activities to occur in a portable manner. Additionally, to discriminate from one wavelength to another wavelength, the example transmission-based particle measurement system 150 of FIG. 1B employs the optical spectrometers (OSs) 162a, 162b, such as the Ocean Optics HR4000 CG-UV-NIR. Although the methods and apparatus described herein will focus on the example of FIG. 1A, such descriptions are by way of example and not limitation.

Figure 1C:
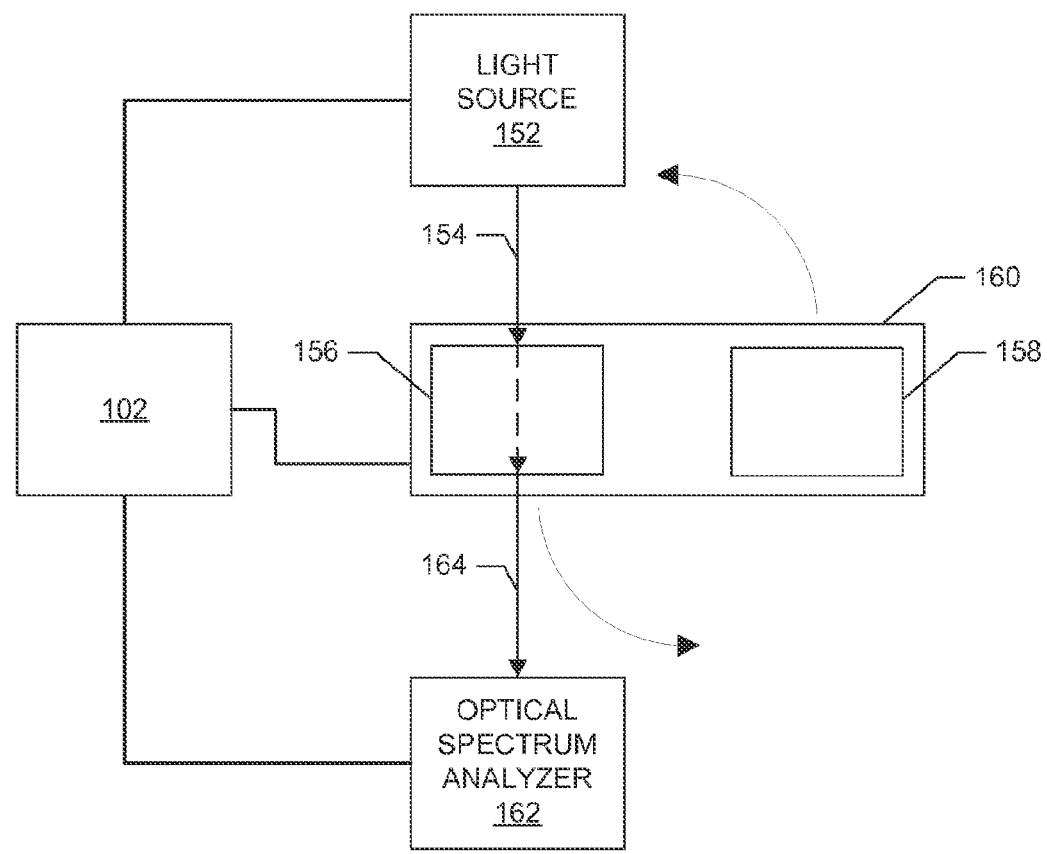

FIG. 1C illustrates yet another example transmission-based particle measurement system 175. The illustrated example of FIG. 1C is substantially similar to the system 150 shown in FIG. 1B and similar elements will maintain similar labels. In the illustrated example of FIG. 1C, a broadband light source 152 provides an incident light beam 154 directed at a sample under test 156. The example broadband light source 152 may include, but is not limited to a highly stable, stabilized solid-state light source and/or other broadband light source. The example sample under test 156 may include a container, crucible and/or other optically transmissive container that holds particles to be measured and/or that holds the control sample, as described above. The control sample 158 may hold the suspension fluid, and both the sample under test 156 and control sample 158 may be interchanged by, for example, rotating sample holder 160 by 180 degrees. Rotation of the example holder 160 may occur after an example OS 162 scans a transmitted beam 164 for one or more wavelengths of interest (e.g., a sweep of wavelengths of interest). In operation, transmission versus wavelength measurements are first performed for the particles in the test sample, then the samples are interchanged by moving or rotating the example holder 160 for the purpose of measuring transmission versus wavelength through the control sample.

Figure 2:
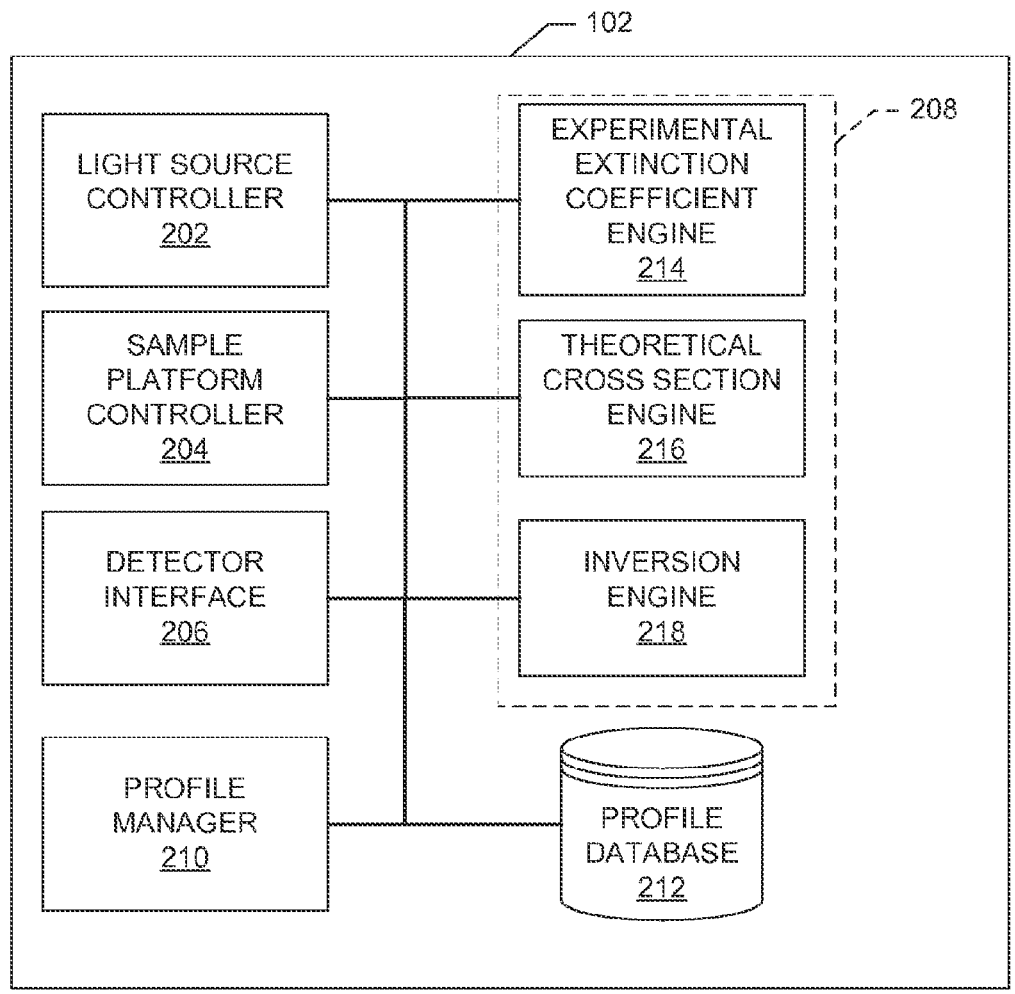
FIG. 2 is a block diagram of an example transmission measurement controller that may be implemented by the example transmission-based particle measurement systems of FIGS. 1A, 1B and 1C.

FIG. 2 illustrates an example transmission measurement controller 102 in further detail. In the illustrated example of FIG. 2, the transmission measurement controller 102 includes a laser controller 202, a sample platform controller 204, a detector interface 206, calculation engines 208, and a profile manager 210 communicatively connected to a profile database 212. In example circumstances where the example transmission-based particle measurement system 150 of FIG. 1B is employed, the light source controller may be, instead, an example controller for the OS 162 and broadband light source 152. The example calculation engines 208 include an experimental extinction coefficient engine 214, a theoretical cross-section engine 216 and an inversion engine 218. In operation, the example light source controller 202 sets a wavelength parameter for the example variable wavelength laser 104 and/or other characteristics of the source laser light 108. For example, in addition to setting the output wavelength, the light source controller 202 may set an output power, a polarization and/or a pulse duration for the example variable wavelength laser 104.

The example platform controller 204 controls as rotation angle for the example motor controlled rotating platform 130 shown in FIG. 1A. As described above, in the event that any given sample under test is to be moved from Beam A 126a to Beam B 126b, or vice versa, the example platform controller 204 engages one or more motors to interchange the test sample with the control sample. The example detector interface 206 provides signal conditioning for one or more detector amplifiers 142a, 142b. Additionally, in the event that one or more detectors do not employ a matched amplifier, the example detector interface 206 may receive detector input directly.

The example calculation engines 208 facilitate one or more calculations using the measured data collected after each sample of interest is subjected to one or more scans by the example variable wavelength laser 104. As described above, the variable wavelength laser 104 is controlled by the laser controller 202 to emit a beam of laser energy at a starting wavelength ($\lambda_{START}$), dwell for a period of time to allow one or more detectors 136a, 136b, 140a, 140b to obtain a transmission measurement, and increment the laser wavelength ($\lambda$) by a step size for another measurement. This process repeats until the finishing wavelength ($\lambda_{FINISH}$) is reached (a first sweep). After switching the example containers 132, 134 or otherwise switching Beam A 126a and Beam B 126b to strike the opposite containers (thereby allowing the containers to remain motionless), a sweep from ($\lambda_{START}$) to ($\lambda_{FINISH}$) (a second sweep) is repeated as part of the balancing measurement techniques. The collected data (i.e., the first and second sweep) is processed by the example calculation engines 208 to determine one or more particle sizes in the sample under test, an absolute number (count) of particles of each size, one or more geometric indications of the detected particles (e.g., a major-axis, a minor-axis, etc.), a particle density value of the sample under test and/or a particle-size distribution of a sample under test.

To determine one or more particle sizes in the sample under test and/or to determine a particle density and/or particle count value of the sample under test, the example calculation engines 208 employ the experimental extinction coefficient engine 214 to calculate an extinction coefficient as a function of wavelength. In particular, the transmission through the sample is a function of particle size and density, which is further related to the total extinction cross section $\sigma(\lambda)$. While the relationship between transmission and a corresponding wavelength provides information related to particle size, the example theoretical cross-section engine 216 is employed to obtain improved sensitivity and resolution when combined and applied to a mathematical inversion via the inversion engine 218. The example theoretical cross-section engine 216 may employ Mie techniques to reveal the size dependence of light transmission by particles, and includes a complete analytical solution of Maxwell's equations for the transmission of electromagnetic radiation by spherical particles. Additionally or alternatively, the example theoretical cross-section engine 216 may employ other theoretical techniques but not, limited to a discrete dipole method(s) and finite element method(s). While an initial assumption that each particle is of spherical shape, the Mie theory may be employed to account for geometries that have more than one dimension (e.g., a cylinder length and/or diameter, non-spherical particles, etc.). In circumstances Where a particle under test has one or more dimensions, separate values for these dimensions will be detected, thereby indicating one or more signature geometric characteristics for the sample under test. Generally speaking, the extinction coefficient (e.g., a first parameter) equals the product of the extinction cross section (e.g., a second parameter) and the particle density (e.g., a third parameter). As such, knowledge, derivation and/or calculation of two parameters may yield the missing parameter.

Figure 3:
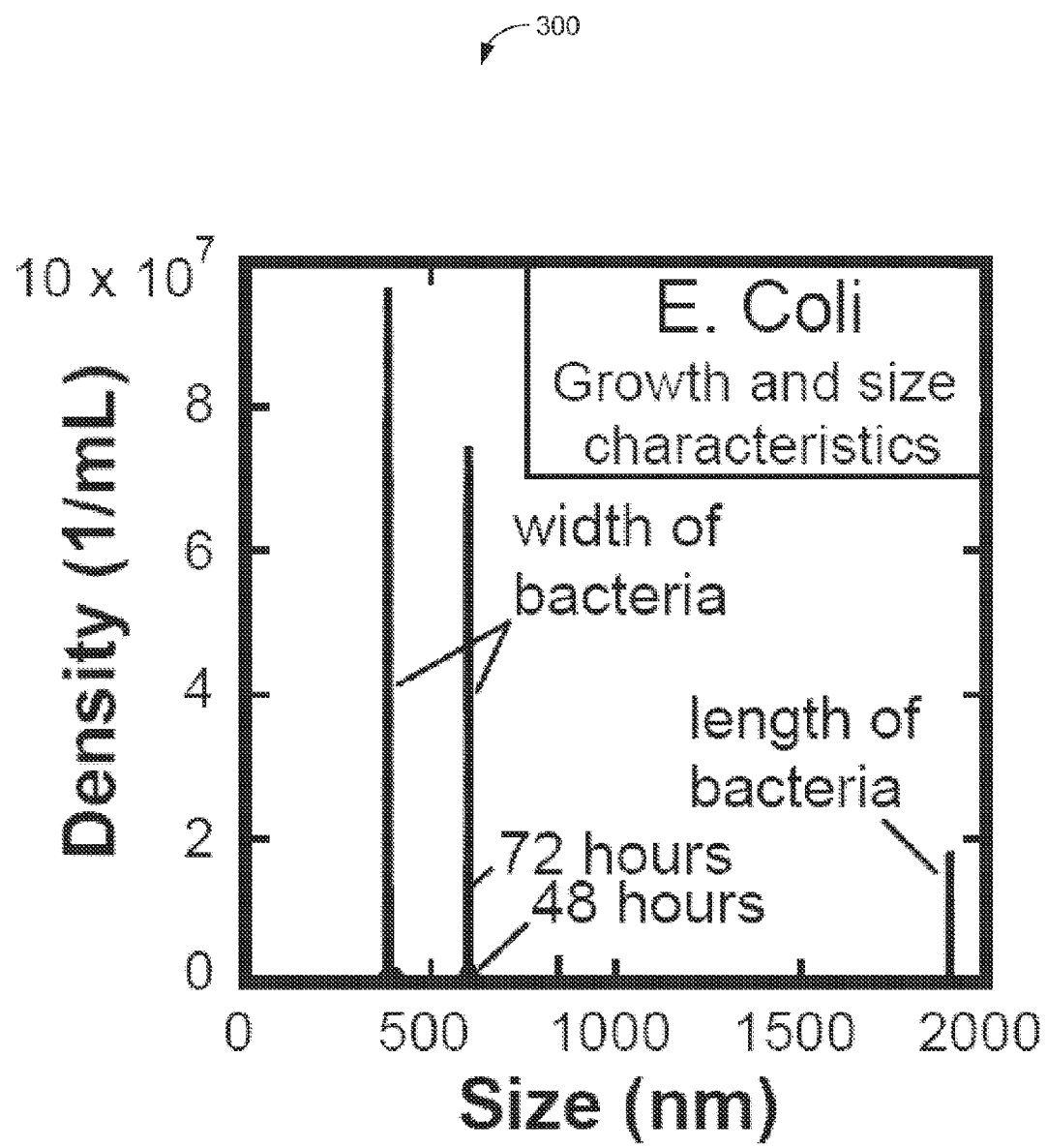
FIG. 3 is an example plot of particle density versus bacteria particle size for transmission-based measurement techniques.

Alternate modeling may be applied to the theoretical cross-section engine 216 and/or the inversion engine 218 to develop one or more libraries of signature patterns, which may be stored and/or recalled from the example profile database 212. Generally speaking, while a spherical particle shape assumption may accurately identify particle sizes and/or particle distribution within a solution, one or more profiles may be used to identify the types of particles. For example, particle sizes of milk colloidals in skim and/or whole milk have been verified with a resolution five times better than dynamic light scattering techniques by using a spherical model. On the other hand, the *E. Coli* bacteria and bacteriophages are better modeled as cylinders haying a diameter and length. As the example transmission-based particle measurement systems 100, 150 and/or 175 are used, an increasing number of signatures for biological systems, viruses and/or proteins may be stored as one or more profiles in the example profile database 212. For instance, the illustrated example plot 300 of FIG. 3 illustrates *E. Coli* bacteria at an early stage and at a subsequent stage in which bacteria multiplication has occurred.

Building further upon the relationship between the extinction coefficient, the extinction cross section and the particle density, one or more alternate techniques may be applied to determine missing data associated with a sample under test. In another example, the extinction coefficients may be obtained via measurement and, instead of applying Mie theory to determine the corresponding extinction cross sections, the example profile database 212 may be queried to obtain extinction cross sections for known viruses, bacteria, particles having a known index of refraction and/or particles having a known geometry. Based on the measured extinction coefficients and the extinction cross sections obtained from the example profile database 212, an inversion may be applied to obtain a corresponding particle density of the sample under test.

In yet another example, in the event that a sample under test has a known particle density, the corresponding extinction cross section may be determined without applying Mie techniques by measuring the sample under test to obtain the extinction coefficients and then dividing them by the known particle density. Without limitation, this process may be repeated any number of times to build a more robust library (e.g., stored in the example profile database 212) of extinction cross section values as a function of wavelength for each particle type. Further still, for circumstances in which the sample under test has a known geometry and density, the corresponding index of refraction and/or dielectric constant of the sample under test may be determined (as a function of wavelength) by measuring the sample for the extinction coefficients and then dividing them by the known geometry and density.

While the example transmission-based particle measurement system 100, 150, 175 and transmission measurement controller 102 of FIGS. 1A, 1B, 1C and 2 have been shown to identify particle sizes and densities of materials suspended in a solution, one or more of the elements and/or devices illustrated in FIGS. 1A, 1B, 1C and 2 may be combined, divided, re-arranged, omitted, eliminated and/or implemented in any other way. Further, the example transmission measurement controller 102, the first mirror array 106, the variable wavelength laser 104, the linear slide 110, the motor controlled rotating platform 130, the first photodetector 136a, the second photodetector 136b, the second mirror array 138, the third detector 140a, the fourth detector 140b, the first detector/amplifier 142a, the second detector/amplifier 142b, the light source 152, the rotating sample holder 160, the optical spectrometers 162, 162a, 162b, the light source controller 202, the sample platform control ter 204, the detector interface 206, the calculation engines 208, the profile manager 210, the profile database 212, the experimental extinction coefficient engine 214, the theoretical cross section engine 216 and/or the inversion engine 218 of FIGS. 1A, 1B, 1C and 2 may be implemented by hardware, software and/or firmware. Thus, for example, any of the example transmission measurement controller 102, the first mirror array 106, the variable wavelength laser 104, the linear slide 110, the motor controlled rotating platform 130, the first photodetector 136a, the second photodetector 136b, the second mirror array 138, the third detector 140a, the fourth detector 140b, the first detector/amplifier 142a, the second detector/amplifier 142b, the light source 152, the mutating sample holder 160, the optical spectrometers 162, 162a, 162b, the light source controller 202, the sample platform controller 204, the detector interface 206, the calculation engines 208, the profile manager 210, the profile database 212, the experimental extinction coefficient engine 214, the theoretical cross section engine 216 and/or the inversion engine 218 may be implemented by one or more circuit(s), application specific integrated circuit(s) (ASIC(s)), programmable logic device(s) (PLD(s)), and/or field programmable logic device(s) (FPLD(s)), etc. When any of the appended apparatus claims are read to cover a purely software and/or firmware implementation, at least one of the example transmission measurement controller 102, the first mirror array 106, the variable wavelength laser 104, the linear slide 110, the motor controlled rotating platform 130, the first photodetector 136a, the second photodetector 136b, the second mirror array 138, the third detector 140a, the fourth detector 40b, the first detector/amplifier 142a, the second detector/amplifier 142b, the light source 152, the rotating sample holder 160, the optical spectrometer 162a, 162b, the light source controller 202, the sample platform controller 204, the detector interface 206, the calculation engines 208, the profile manager 210, the profile database 212, the experimental extinction coefficient engine 214, the theoretical cross section engine 216 and/or the inversion engine 218 are hereby expressly defined to include a tangible medium such as a memory, DVD, CD, etc. storing the software and/or firmware. Further still, the example transmission measurement controller 102, the first mirror array 106, the variable wavelength laser 104, the linear slide 110, the noire controlled rotating (or otherwise movable) platform 130, the first photodetector 136a, the second photodetector 136b, the second mirror array 138, the third detector 140a, the fourth detector 140b, the first detector/ amplifier 142a, the second detector/amplifier 142b, the light source 152, the rotating (or otherwise movable) sample holder 160, the optical spectrometer 162a, 162b, the light source (e.g., laser) controller 202, the sample platform controller 204, the detector interface 206, the calculation engines 208, the profile manager 210, the profile database 212, the experimental extinction coefficient engine 214, the theoretical cross section engine 216 and/or the inversion engine 218 of FIGS. 1A, 1B, 1C and 2 may include one or more elements, processes and/or devices in addition to, or instead of, those illustrated in FIGS. 1A, 18, 1C and 2, and/or may include more than one of any or all of the illustrated elements, processes and devices.

FIGS. 4 through 6 and 8 illustrate example processes that may be performed to implement the example transmission-based particle measurement systems 100, 150, 175 and/or the example transmission measurement controller 102 of FIGS. 1A, 1B, 1C and 2. The example processes of FIGS. 4 through 6 and 8 may be carried out by a processor, a controller and/or any other suitable processing device. For instance, the example processes of FIGS. 4-6 and 8 may be embodied in coded instructions stored on any tangible computer-readable medium such as a flash memory, a CD, a DVD, a floppy disk, a read-only memory (ROM), a random-access memory (RAM), a programmable ROM (PROM), an electronically-programmable ROM (EPROM), and/or an electronically-erasable PROM (EEPROM), an optical storage disk, an optical storage device, magnetic storage disk, a magnetic storage device, and/or any other medium that can be used to carry or store program code and/or instructions in the form of machine-readable instructions or data structures, and that can be accessed by a processor, a general-purpose or special-purpose computer, or other machine with a processor (e.g., the example processor platform P100 discussed below in connection with FIG. 10). Combinations of the above are also included within the scope of computer-readable media. Machine-readable instructions comprise, for example, instructions and/or data that cause a processor, a general-purpose computer, a special-purpose computer, or a special-purpose processing machine, to implement one or more particular processes. Alternatively, some or all of the example processes of FIGS. 4-6 and 8 may be implemented using any combination(s) of ASIC(s), PLD(s), FPLD(s), discrete logic, hardware, firmware, etc. Also, one or more operations of the example processes of FIGS. 4-6 and 8 may instead be implemented manually or as any combination of any of the foregoing techniques, for example, any combination of firmware, software, discrete logic, and/or hardware. Further, many other methods of implementing the example operations of FIGS. 4-6 and 8 may be employed. For example, the order of execution of the blocks may be changed, and/or one or more of the blocks described may be chanced, eliminated, subdivided, or combined. Additionally, any or all of the example processes of FIGS. 4-6 and 8 may be carried out sequentially and/or carried out in parallel by, for example, separate processing threads, processors, devices, discrete logic, circuits, etc.

Figure 4:
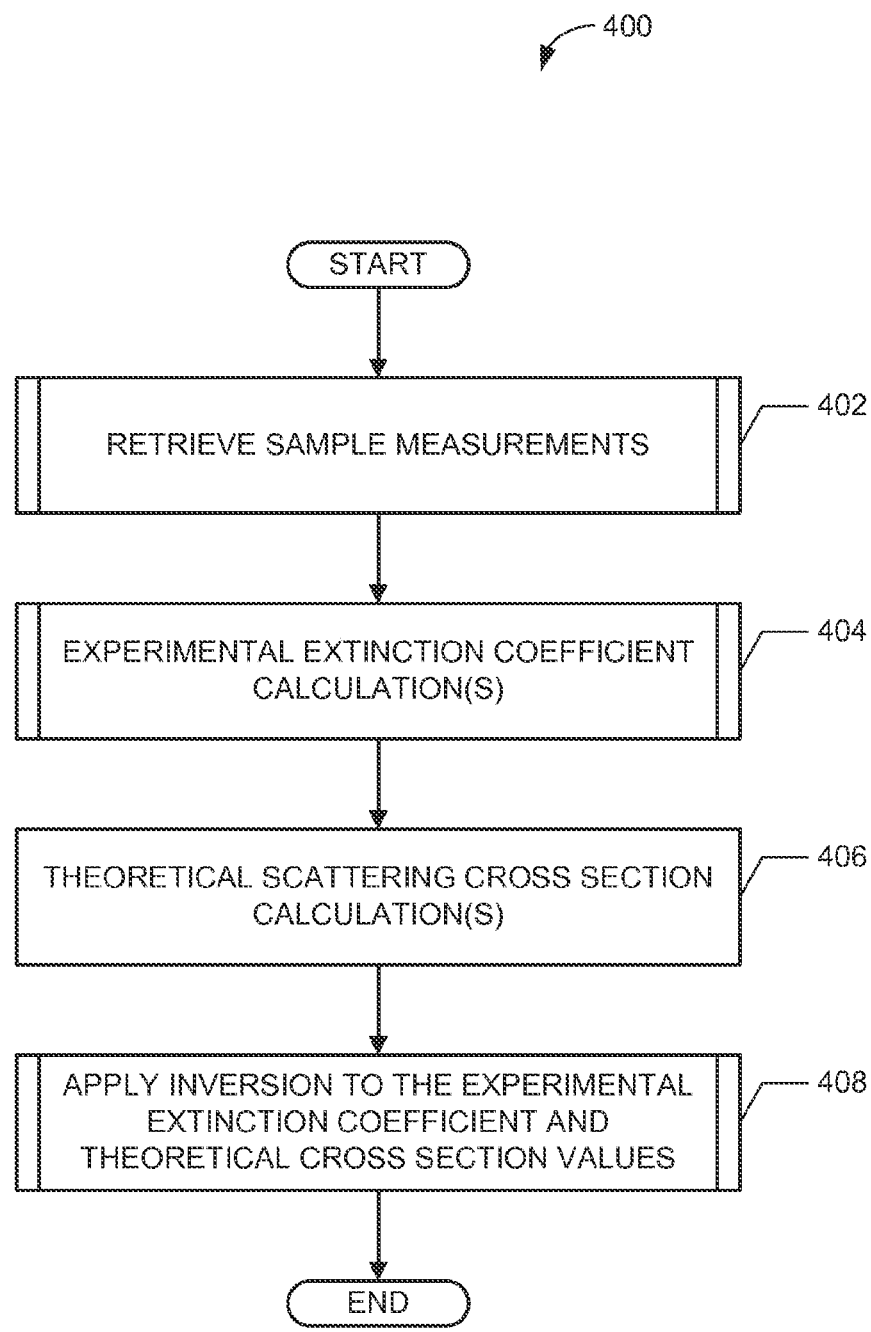
FIGS. 4-6 and 8 are example processes that may be carried out using tangible machine readable instructions to implement the example transmission-based particle measurement systems of FIGS. 1A, 1B and 1C.

The example process 400 of FIG. 4 begins with retrieving sample measurements from a particle sample under study and sample measurements from a control sample (block 402). As described above, by comparing the two sets of data obtained via the balance measuring techniques (i.e., one set for the particle sample and one set for the control sample and repeating for alternate beams), any differences in detector characteristics, amplifier characteristics and/or container characteristics may be eliminated, thereby improving a measure of the minimum signal that can be distinguished above noise levels (sensitivity), and improving a measure of observable detail (resolution). Additionally, by comparing the particle sample with the control sample, any effect of the suspension fluid on the transmission characteristics can be eliminated. To calculate a total extinction coefficient as a function of wavelength $\alpha(\lambda)$, the example experimental extinction coefficient engine 214 calculates the ratios between the particle sample and the control sample (block 404). The theoretical cross-section engine 216 determines a scattering cross-section using, but not limited to Mie techniques, other theoretical techniques and/or a database of cross sections to reveal one or more size dependencies of light transmission by the particles in the particle sample (block 406). Improved sensitivity and resolution is also realized by using the experimentally determined extinction coefficient and the theoretically determined scattering cross-section with a mathematical inversion (block 408). The mathematical inversion may include, but is not limited to a Fredholm Integral, as shown in Equation 1.

$$I(\lambda) = \int_{r_{MIN}}^{r_{MAX}} K(\lambda, r) f(r) dr. \qquad \text{Equation 1}$$

In the illustrated example Equation 1 when applied to the transmission techniques described herein, $I(\lambda)$ represents the extinction coefficient $\alpha(\lambda)$ as a function of wavelength ($\lambda$) and $f(r)$ represents the particle size distribution as a function of particle radius. The kernel, $K(\lambda,r)$ is the theoretical extinction cross section as a function of wavelength ($\lambda$) and radius ($r$). The complex index of refraction as a function of wavelength is an input to the calculation of the kernel $K(\lambda,r)$. Each of $r_{MIN}$, $r_{MAX}$ and dr are referred to herein as resolution parameters that may affect a resolution of particle size distribution. The representation $K(\lambda,r)$ is sometimes referred to as an inversion kernel function because it contains all possible theoretical extinction cross-sections for all wavelengths of scattering light and all particle sizes of interest. To obtain particle size and count information, a particle size distribution (PSD) is determined from Equation 1, which is represented by $f(r)$. Generally speaking, the experimental extinction coefficient engine 214 facilitates calculation of $I(\lambda)$, the theoretical cross-section engine 216 facilitates calculation of $K(\lambda,r)$, and the PSD can be solved by way of a mathematical transformation, such as, but not limited to Laplace transforms, Fourier transforms and/or matrix inversion techniques.

Inversion accuracy may be influenced by selected resolution parameters, such as $r_{MIN}$, $r_{MAX}$ and dr. In the event that a resolution is selected during the inversion that is too low, information from the sample measurements may be lost. For example, the extinction coefficient $I(\lambda)$ would contain more information than what is extracted from the inversion. On the other hand, in the event that a resolution is selected during the inversion that is too high, numerical artifacts may result, such as multiple peaks where fewer actual peaks should exist. In this example circumstance, $I(\lambda)$ would not contain the required information needed to achieve the resolution and a substantial error may result. While example Equation 1 may represent art integral form having a step size dr that can be infinitely small, numerically calculating Equation 1 with real values reflects a resolution $\Delta r$ equal to $r_{MAX}$ minus mss $r_{MIN}$ divided by a whole number of points. For example, for a range from $r_{MIN}$ of 1 nm to $r_{MAX}$ of 1001 nm and 1000 points, the corresponding resolution $\Delta r$ would be 1 nm.

Resolution parameter selection may be based on heuristics, input from the example profile manager 210 and/or based on the type of particle(s) believed to be in the sample under test.

For example, if multiple-size particles are present, the inversion resolution may need to be changed. For example, setting the inversion resolution, Δr, or particle diameter step size, to a multiple of the resolution of the experimental data ($\lambda_{STEP}$), or wavelength step size, may remove spurious inversion peaks. This multiple may be a factor of two. Resetting the inversion resolution may also be indicated in other circumstances, including a case where particles homogeneous in size are present.

Figure 5:
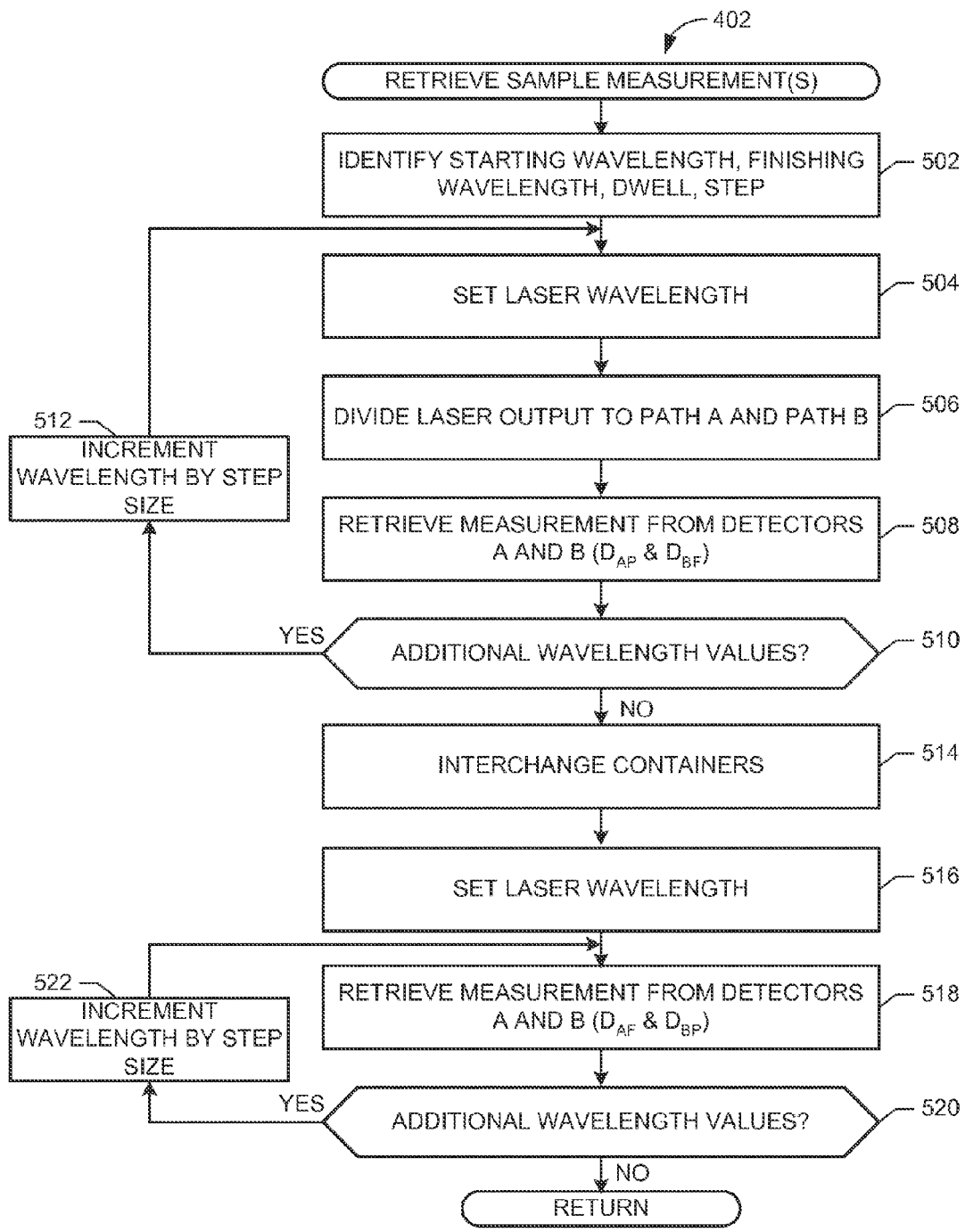

The example process 402 of FIG. 5 retrieves sample Measurements from the particle sample under study and sample measurements from the control sample, such as pure and/or deionized water. In the illustrated example of FIG. 5, the transmission measurement controller 102 identifies a starting laser wavelength ($\lambda_{START}$), a final laser wavelength ($\lambda_{FINISH}$), a wavelength step size ($\lambda_{STEP}$) and a dwell time for each step (block 502). Such settings may be stored in a profile, such as the example profile manager 210 shown in FIG. 2 and/or one or more laser control settings may be adjusted by a user. The identified laser settings are provided to the example laser controller 202 to allow one or more sequences of laser wavelengths to be emitted during the testing of the particle sample of interest (block 504) (e.g., during the first sweep). To illustrate, the example laser controller 202 configures the example variable wavelength laser 104 to emit laser radiation at a starting wavelength ($\lambda_{START}$) for the desired dwell period and, after a measurement is acquired of laser radiation transmitted through each container (e.g., sample A 132 and sample B 134); the example laser controller 202 adjusts the laser wavelength based on the desired step size ($\lambda_{STEP}$). This sequence of laser emission, dwell time, and wavelength adjustment repeats from the starting wavelength to the final wavelength.

The example sample platform controller 204 may control one or more devices within the example first mirror array 106 and/or the example second mirror array 138, such as a position of the example linear slide 110, broadband mirrors 112, 118, 1311, fused silica optical fiats 114a, 114b and/or the example beam dumps 116. The example sample platform controller 204 may also rotate a position of sample A 132 and sample B 134 on the rotating sample holder 128 to allow the divided laser source energy to strike each sample with Beam A 126a and Beam B 126b, respectively (block 506). However, rotation of the samples 132, 134 may occur after the first sweep is complete. Without limitation, the example first mirror array 106 and second mirror array 138 may be adjusted to direct Beam A 126a and Beam B 126b toward the opposite containers after the first sweep in-between each wavelength scan, thereby allowing the containers 132, 134 to remain motionless. As described above, sample A 132 may hold the particle sample under test while sample B 134 may hold the control sample (e.g., a suspension fluid without any particle matter therein).

Eat it of incident Beam A 126a and B 126b strikes each sample A 132 and B 134 to allow the laser energy to traverse through the containers. While some of the laser energy is absorbed, reflected and/or scattered by each sample, a portion of the laser energy from each of Beam A 126a and Beam B 126b is transmitted through each container at the original angle of incidence (i.e., zero degrees) and strikes each of the first photodetector 136a (photodetector A) and the second photodetector 136b (photodetector B). Measurements from each photodetector are retrieved and saved as $D_{AP}$ and $D_{BF}$ (block 508), where $D_{AP}$ represents the resulting signal detected by photodetector A after transmission through the particle sample ($_p$), and $D_{BF}$ represents the resulting signal detected by photodetector B after transmission through the control fluid sample ($_F$). If the finishing wavelength ($\lambda_{FINISH}$) has not been reached (block 510), then the example laser controller 202 increments the laser wavelength (h) by the desired step size (block 512).

After a number of iterations of laser emission, dwell, measurement, and incrementing the laser wavelength from ($\lambda_{START}$) to ($\lambda_{FINISH}$) (e.g., the first sweep), the example sample platform controller 204 energizes the motor controlled sample holder to interchange the samples so that Beam A 126a strikes sample B 134 (i.e., the control sample) and Beam B 126b strikes sample A 132 (i.e., the particle sample under test) (balance measurement) (block 514). The example laser controller 202 sets the variable wavelength laser 104 to the starting wavelength ($\lambda_{START}$) (block 516) and measurements are obtained from photodetector A 136a and photodetector B 136b to obtain $D_{AF}$ and $D_{BF}$, respectively (block 518). $D_{AF}$ represents the resulting signal detected by photodetector A after transmission through the control fluid sample ($_F$) 134, and $D_{BP}$ represents the resulting signal detected by photodetector 11 after transmission through the particle sample ($_p$) 132. IF additional adjustments to the example variable wavelength laser 104 are needed during one or more steps from ($\lambda_{START}$) to ($\lambda_{FINISH}$) (block 520), then the example laser controller 202 makes the adjustment and increments the wavelength of emitted laser light by the step size (block 522).

Figure 6:
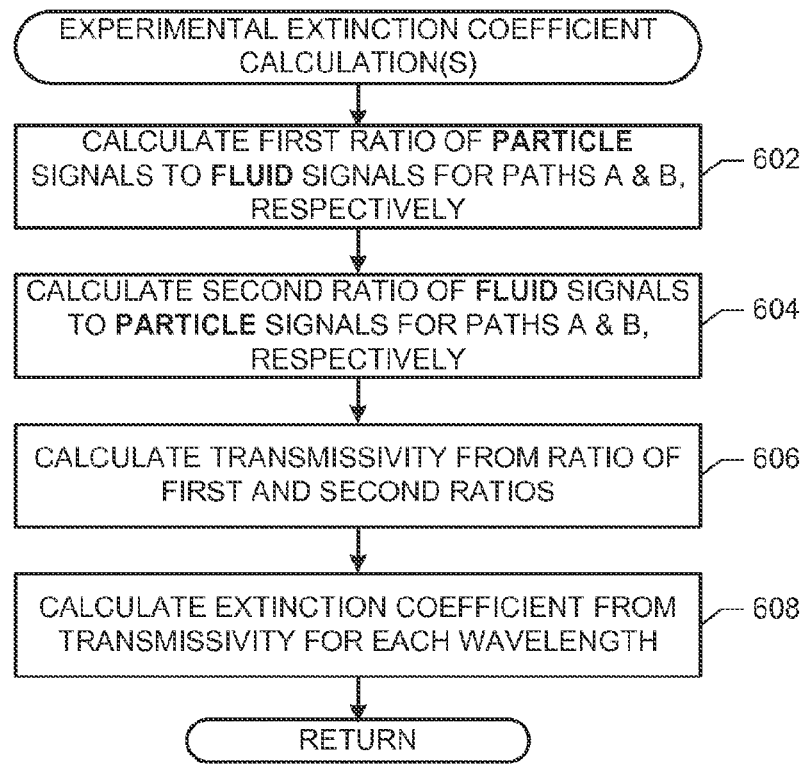

In the example process 404 of FIG. 6, the experimental extinction coefficient engine 214 calculates a first ratio of particle signal to fluid signal for Beam A 126a and Beam B 126b. As described above, the example variable wavelength laser 104 output 108 is split into two beams having similar powers $P_A$ and $P_B$ and similar polarization values. Prior to measuring the transmission of a test sample, the entire measurement process and ratio calculations described below are performed with no samples and/or identical samples to ensure that the system 100, 150, 175 is balanced. The fractions of input light power transmitted through each container are represented by Equations 2 and 3 shown below.

$$D_{AP}(\lambda) = \in_A(\lambda) T_P(\lambda) T_F(\lambda) P_A(\lambda) \qquad \text{Equation 2.}$$

$$D_{BF}(\lambda) = \in_B(\lambda) T_F(\lambda) P_B(\lambda) \qquad \text{Equation 3.}$$

In the illustrated example Equation 2 and Equation 3, $D_{AP}$ represents the resulting signal detected by photodetector A after transmission through the particle sample (p) (test sample), $D_{BF}$ represents the resulting signal detected by photodetector B after transmission through the suspension fluid ($_F$) (control sample), $\in_A$ represents the efficiency of photodetector A 136a, $\in_B$ represents the efficiency of photodetector B 136b, $T_P(\lambda)$ represents the fraction of input light power transmitted by the particles at a given wavelength, and $T_F(\lambda)$ represents the fraction of input light power transmitted through the suspension fluid at the given wavelength. As described above, the particle sample ($_p$) And the suspension fluid ($_F$) containers are interchanged (balance measuring) so that another set of measurements therethrough can be made. Similar to Equations 2 and 3, the fractions of input light power transmitted through the particle sample ($_p$) and suspension fluid ($_F$) are represented by Equations 4 and 5 shown below.

$$D_{AF}(\lambda) = \in_A(\lambda) T_F(\lambda) P_A(\lambda) \qquad \text{Equation 4.}$$

$$D_{BP}(\lambda) = \in_B(\lambda) T_P(\lambda) T_F(\lambda) P_B(\lambda) \qquad \text{Equation 5.}$$

In the illustrated example Equation 4 and Equation 5, $D_{AF}$ represents the resulting signal detected by photodetector A after transmission through the suspension fluid ($_F$) (control sample) and $D_{BP}$ represents the resulting signal detected by photodetector B after transmission through the particle sample ($_p$). The example experimental extinction coefficient engine 214 calculates a first ratio of the particle signals to the suspension fluid signals for Beam A and Beam B, respectively (block 602). Similarly, after the full range of wavelengths are scanned from ($\lambda_{START}$) to ($\lambda_{FINISH}$), the example experimental extinction coefficient engine 214 calculates a second ratio of the suspension fluid signals to the particle signals for Beam A and Beam B, respectively (block 604). The four signals from Equations 2, 3, 4 and 5 as a result of the first sweep of wavelengths and the second sweep of wavelengths from the balance measuring are used to calculate a ratio of ratios R($\lambda$) as shown in Equation 6.

$$R(\lambda) = \frac{\frac{D_{AP}(\lambda)}{D_{BF}(\lambda)}}{\frac{D_{AF}(\lambda)}{D_{BP}(\lambda)}} = (T_p(\lambda))^2. \qquad \text{Equation 6}$$

The transmissivity versus wavelength $T_p(\lambda)$ due to the particles in the particle sample 132 may be computed as shown in Equation 7 (block 606).

$$T_p(\lambda) = \sqrt{R(\lambda)} = \sqrt{\frac{\frac{D_{AP}}{D_{BF}}}{\frac{D_{AF}}{D_{BP}}}} = e^{-\alpha(\lambda)l}. \qquad \text{Equation 7}$$

$$\alpha(\lambda)l = -\ln\left(\frac{\frac{D_{AP}}{D_{BF}}}{\frac{D_{AF}}{D_{BP}}}\right) = -\frac{1}{2}\ln\left(\frac{\frac{D_{AP}}{D_{BF}}}{\frac{D_{AF}}{D_{BP}}}\right). \qquad \text{Equation 8}$$

In the illustrated example of Equation 8, α(λ) represents the extinction coefficient and l represents the path length through the sample (i.e., the length of the light passing through the particle liquid (material), but not the container widths). Example Equation 8 is used to calculate the experimental value of the extinction coefficient at each wavelength. In theory, the extinction coefficient versus wavelength α(λ) due to the particles is related to the total theoretical scattering cross-section $\sigma_i(\lambda)$ of particle type i by Equation 9.

$$\alpha(\lambda) = \Sigma_j \sigma_j(\lambda) n_j \qquad \text{Equation 9.}$$

In the illustrated example Equation 9, $n_j$ is the number of particles per unit volume of type and the summation $\Sigma_j$ is over all particle types. Equation 8 illustrates calculating the extinction coefficient from the data for each wavelength (block 608). Equation 9 is inverted to obtain the number of particles per unit volume $n_j$ of each type j. If there is a continuum of particle sizes, then the extinction coefficient is represented as shown below in example Equation 9b, where n(r) is the particle size distribution.

$$\alpha(\lambda) = \int \sigma(\lambda,r)n(r)dr \qquad \text{Equation 9b.}$$

Briefly returning to FIG. 4, the example theoretical cross-section engine 21*ti* employs one or more theoretical techniques such as, but not limited to Mie theory and/or a database to model the total cross section of the particle sample under test (block 406). Generally speaking, Mie theory is a complete analytical solution of Maxwell's equations for the scattering of electromagnetic radiation by spherical particles. While Mie theory techniques typically perform with optimum results when the ratio of the particle diameter to the incident laser wavelength are on the order of unity, the methods and apparatus described herein may be employed to determine a major and minor axis of the particles under study by, in part, employing a range of wavelengths. Unlike particle sizing techniques that utilize scattering, in which the laser wavelength (λ) is fixed and the scattering angle (θ) is varied or scattered light is measured at one or more fixed angle other than zero, the methods and apparatus described herein utilize transmission behavior of the laser energy, in which the laser wavelength (λ) is varied and transmitted light is measured at an angle (θ) fixed at zero with respect to the incident light detection. As described above, monitoring the transmission of the laser energy improves size, density, count and/or geometry determinations by utilizing a single photodiode for each incident (i.e., zero angle with respect to the incident light direction) laser beam, rather than an array of photodiodes that are typically required when employing scattering techniques. Generally speaking, scattering techniques can never capture all of the scattered light, whereas the transmitted tight signal is always sensitive to all of the scattered light. The transmitted light signal is ultimately a function of light scattered at all directions, but scattering techniques, including dynamic light scattering and diffraction, detect only a fraction of the scattered light. Generally speaking, as a number of additional photodiodes are added to a measurement system in an attempt to capture more of the scattered light, a corresponding uncertainty in the measured data accumulates, which may lower any resulting sensitivity and/or resolution. By applying Mie theory techniques to light transmission detection at multiple wavelengths and at a zero degree scattering angle, a theoretical extinction cross-section versus wavelength σ(λ,r) may be obtained for each particle radius by first calculating Mie coefficients, as shown in Equation 10.

$$\sigma(\lambda, r) = \frac{2\pi}{k^2} \sum_{n-1}^{\infty} (2n + 1)(a_n(\lambda, r) + b_n(\lambda, r)). \qquad \text{Equation 10}$$

In the illustrated example of Equation 10, $a_n$ and $b_n$ are the Mie coefficients, and the extinction cross-section σ(λ,r) may be defined as shown in Equation 10. In Equation 10, k=2π/λ.

In some examples the Mie calculations may be performed by the theoretical cross-section engine 216 by way of one or more applications, such as MIEV0 by Warren J. Wiscombe and one or more graphical outputs of the Mie calculations may be performed by the theoretical cross-section engine 216 to illustrate general particle size trends and/or occasions where the incident laser light wavelength is at or near the size of the corresponding particle diameters. Generally speaking, plotted Mie calculations illustrate major and minor oscillatory behavior, peaks and/or valleys depending on the particle size, the index of refraction of the particle and/or the index of refraction of the surrounding medium (e.g., fluid, gas, spray, etc.). Additionally, relatively small oscillatory ripples may occur when transmitted laser light paths interfere with each other. Ripples can occur because some light energy is transmitted through each particle (e.g., sphere) with no internal reflections therein along path $P_0$, and some light is transmitted through each particle after internal reflections within the particle that exit in the same direction as $P_0$, but have a different phase and path length, $P_n$. Accordingly, more than one $P_n$ can exist, which may result in observed interference between $P_0$ and any number of $P_n$ paths, thereby showing up as ripples in the extinction cross section σ(λ,r) when plotted.

Using the Mie calculations to infer a particle density as a function of size using data obtained without the balancing techniques described above may provide one or more indications of general particle size, however such results alone may not reveal a range of particle sizes and/or densities of each particle size within the sample under test with a suitable resolution, sensitivity and/or absolute density information. In other words, results from only the Mie calculations using data obtained without proper balancing techniques may be limited in their ability to provide results that enable the accurate identification of particle sizes, geometries and/or an ability to identify a particle type (e.g., viruses, bacteria, proteins, cells, etc.). The methods and apparatus described herein utilize the balance measuring techniques, the Mie calculation results, and the experimental results with a tailored mathematical inversion to enable calculation of any number particle sizes that may be present in the sample under test, in which the resulting sizes have a resolution that is significantly better than scattering-based particle sizing techniques. Additionally, due to, in part, the balance measuring techniques, the methods and apparatus described herein reveal an absolute number of objects in the sample under test rather than a relative number of objects, as provided by scattering-based methods (e.g., dynamic light scattering). Further, the balance measuring techniques facilitate the ability to identify a major and minor axis of non-spherical particles and the ability to distinguish multiple sizes in the sample under test. The balance measurements farther improve a dynamic range and yield a sensitivity that is approximately one million times more sensitive than dynamic light scattering-based methods, as shown in FIG. 7A, and a resolution that is approximately five times better than results achieved with dynamic light scattering-based methods, as shown in FIG. 7B.

Figure 7A:
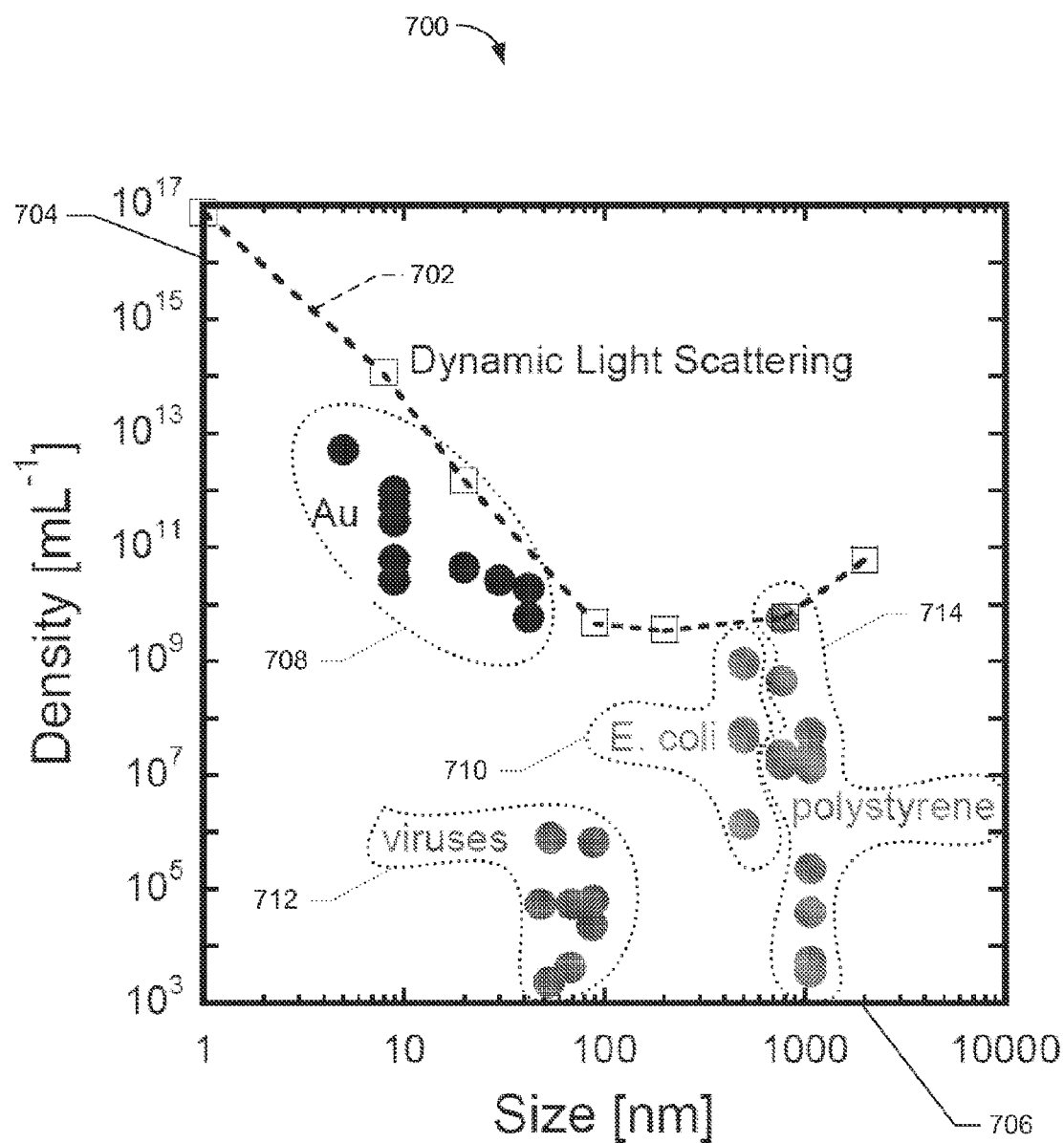
FIG. 7A is a sensitivity comparison plot of particle density versus particle size for scattering-based measurement techniques and transmission-based measurement techniques.

In the illustrated example of FIG. 7A, a technique comparison plot 700 is shown to illustrate capabilities of dynamic light scattering techniques (dashed line 702) and the transmission-based methods and apparatus described herein (see circles in FIG. 7A). The example plot 700 of FIG. 7A includes a y-axis 704 of particle density (concentration) per ML, and an x-axis 706 of particle size in nm. While the results from dynamic light scattering illustrate an ability to distinguish particle concentrations at a lower threshold of approximately $10^9$ particles per mL, the transmission-based methods and apparatus described herein illustrate sensitivities as low as approximately $10^3$ particles per mL. Additionally, the plot 700 illustrates successful application of the transmission-based methods and apparatus described herein to detect gold particles 708, *E. Coli* particles 710, and relatively low concentrations of virus particles 712 and polystyrene particles 714. The methods and apparatus described herein analyze the particle sample under test at a range of wavelengths to expose the sizes, densities, counts and/or geometries of particles that may be present therein.

Figure 7B:
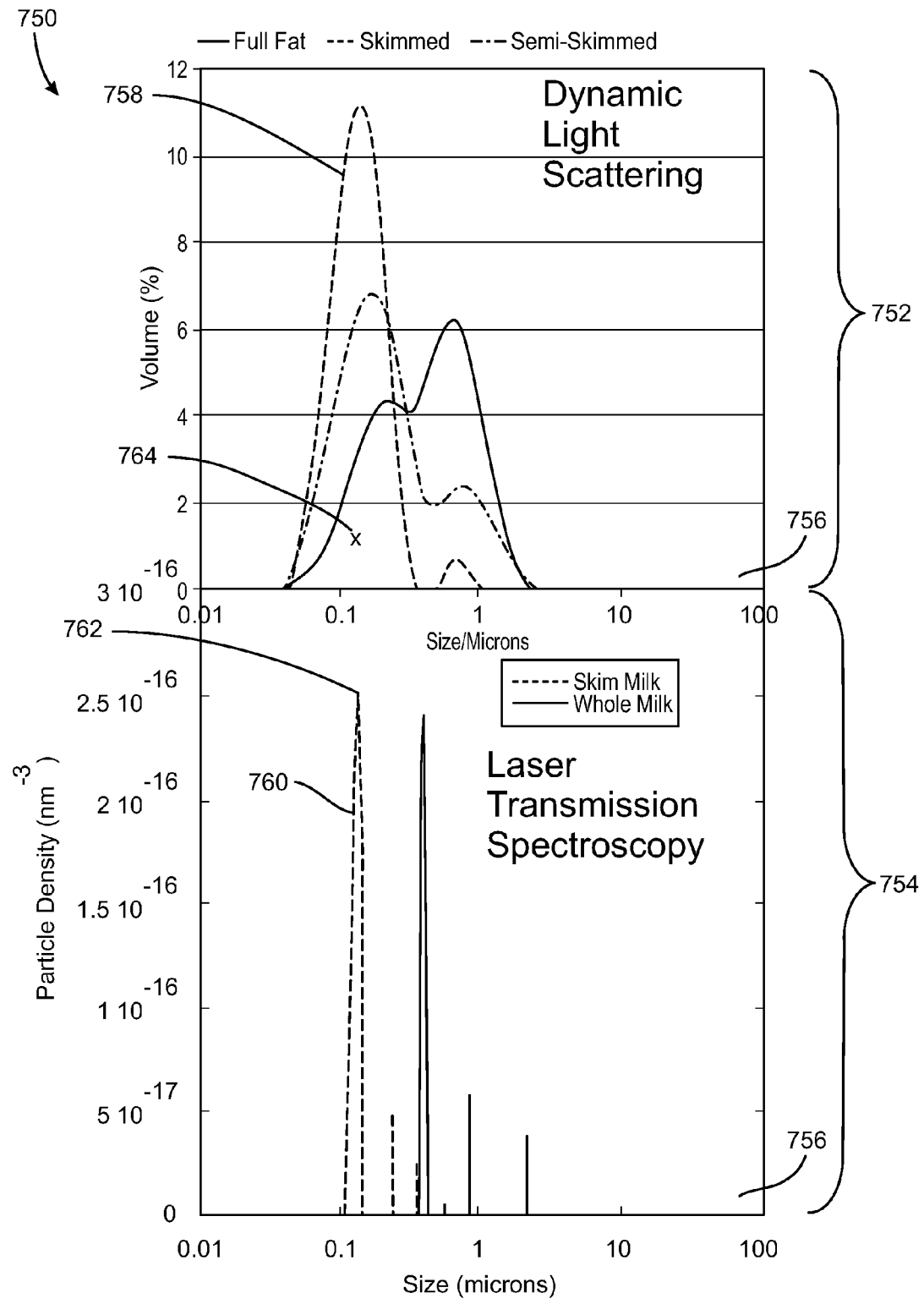
FIG. 7B illustrate example resolution comparison plots of particle density, versus particle size between dynamic light scattering techniques and transmission-based measurement techniques.

In the illustrated example of FIG. 7B, another technique comparison plot 750 is shown to illustrate capabilities regarding resolution for dynamic light scattering techniques (upper plot 752) and the transmission-based methods (lower plot 754) and apparatus described herein. The example dynamic light scattering techniques 752 and transmission-based methods 754 share a similar x-axis 756 to further illustrate improvements to resolution capabilities of the transmission-based methods 754. For example, single spherical casein micelles of milk protein are shown as a peak 758 using dynamic light scattering techniques 752 that are approximately five times wider than a peak 760 derived after employing transmission-based methods 754. As a result, the methods and apparatus described herein related to transmission-based techniques for obtaining suspended particle information allow a finer degree of detail that may not be revealed when employing dynamic light scattering techniques. The example plots 752, 754 of FIG. 7B also illustrate a relative sensitivity improvement of transmission-based techniques over dynamic light scattering. In particular, the peak 760 of spherical casein miscelles of milk protein having a density of $2.5 \times 10^{-16}$ nm$^{-3}$ (762) roughly corresponds to $1.3 \times 10^{-8}$ volume percent (764), thereby indicating a sensitivity factor improvement of approximately one billion.

Figure 8:
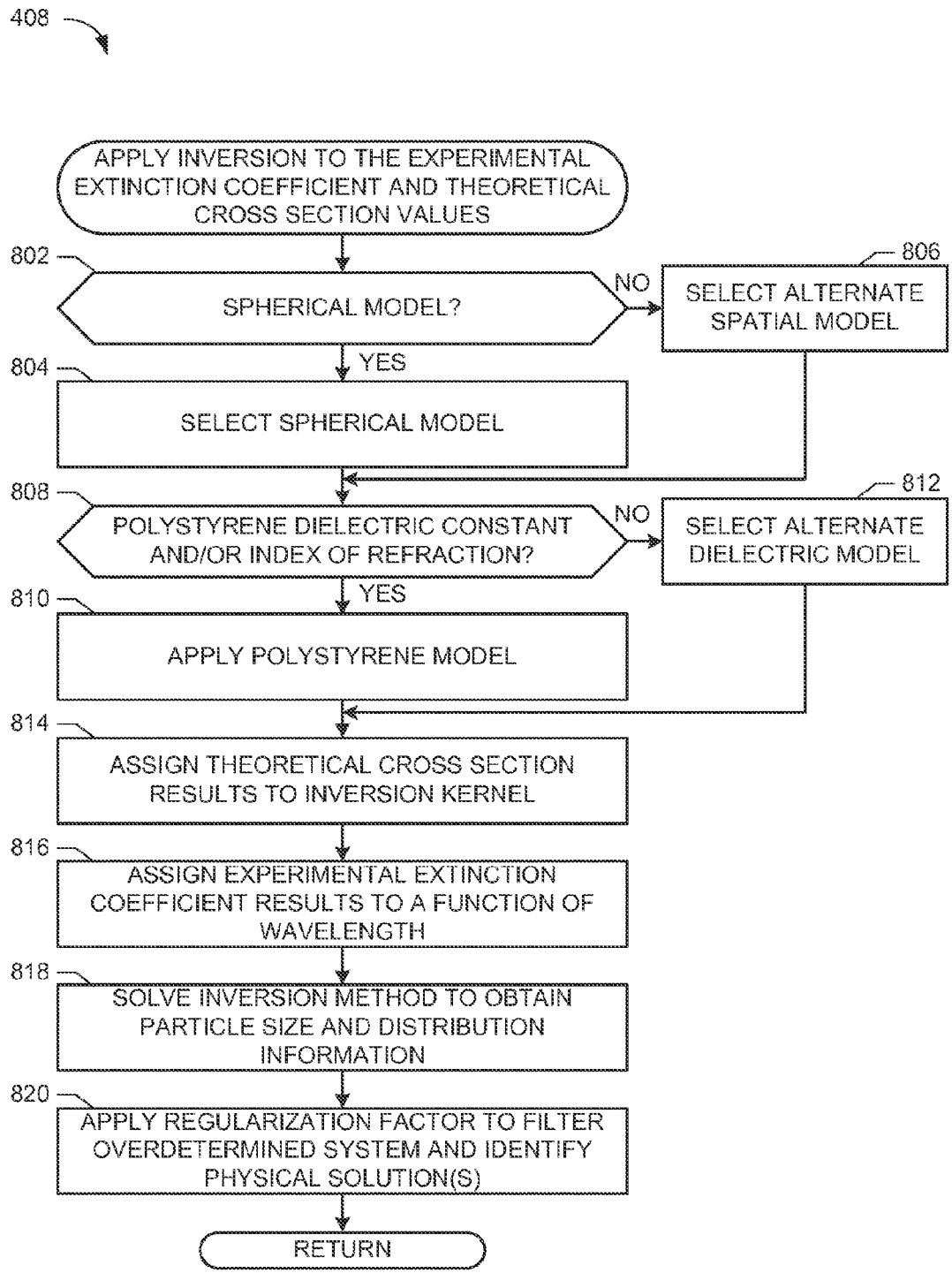

The example process 408 of FIG. 8 begins with selecting a spatial particle size model (block 802) from any number of spatial models that may be available in the example profile manager 210. In some circumstances, a general type of particle present in the particle sample under test may be known, but the specific sizes and/or densities present therein may not be known. For example, if the particle sample under test is known to contain polystyrene spheres from a manufacturing supplier of such spheres, then a spherical spatial model may be selected (block 804). On the other hand, if the general type of particle present in the particle sample under test is not known, the spherical spatial model may be a suitable starting point because it can provide results indicative of a major and minor axis of the particles present. As the example transmission-based particle measurement system 100, 150, 175 is used with different types of particles, the example profile manager 210 may store characteristic spatial signature patterns of the different particle types. Each virus, bacteria and/or manufacturing, particle (e.g., abrasive particles) may exhibit unique spatial signature characteristics that can later be identified with the aid of a selected spatial model (e.g., a rod-shaped model, etc.) and/or stored database model. For circumstances where the particle type is known to be something other than a sphere (block 802), an alternate spatial model may be selected (block 806).

Particles also include a characteristic complex dielectric constant property and/or complex index of refraction. If the particle sample under test is known to contain dielectric properties similar to polystyrene and/or the dielectric constant is generally undetermined (block 808), then a dielectric model associated with polystyrene may be selected to establish a baseline measurement of the particles (block 810). However, if the particles in the sample under test are generally known to have an alternate dielectric value, then an alternate dielectric model may be selected that is more similar to the particles under test (block 812). Major categories of particle types include biological particles, metals and/or oxides.

The example inversion engine 218 assigns, based on the index of refraction and/or dielectric constant of the particles under test, the theoretical results generated by the example theoretical cross-section engine 216 to the inversion kernel function $K(\lambda,r)$ (block 814), and the experimental results generated by the example experimental extinction coefficient engine 214 are assigned to the Fredholm Integral function $I(\lambda)$ at each scanned wavelength ($\lambda$) (block 816). The particle size distribution, n(r), as a function of radius, r, is represented by f(r). The inversion is solved (e.g., example Equation 1) for, f(r), which contains sizing and density information (block 818). In discrete form n(r) is represented by a column vector with elements (j), where each element of the column vector is a particle density. The index j for this column vector is the radius and/or type of the particle. Additionally, the inversion kernel function $K(\lambda,r)$ is represented by an i×j matrix where the i index is the scattering wavelength and the j index is the particle size and/or type. As such, an (i,j) matrix element refers to the extinction cross section (ECSC) of a particle size and/or type j at light wavelength i.

The inversion kernel function $K(\lambda,r)$ is calculated (e.g., MIEV0.f code, etc.) with an assumed radius of the spherical particle having index of refraction (m) at wavelength ($\lambda$) to yield an ECSC. Valid ECSC results are retained as any number of assumed radii are used when solving the Fredholm integral equation (e.g., Equation 1) (e.g., solving for a range of particle sizes that can be expected in a sample particle under test). Additionally, f(r) contains the particle size and count information, and can be visualized as a column matrix with j elements, where the range of j is determined by the limits of integration shown in Equation 1. If one of the elements exists in the example matrix, then a particle exists having the corresponding particle size of the represented matrix position.

To illustrate further, example Equation 1 is the integral of the inversion kernel function $K(\lambda,r)*f(r)$ across a limited range of expected particle sizes to $r_{min}$ to $r_{max}$ (with step size dr) that could exist in the particle sample. During the integration, ECSC values are picked out for particle size(s) that are contained in the particle size distribution f(r) from the kernel $K(\lambda,r)$. The result is an extinction coefficient for a particle sample having size distribution f(r), which is represented as $I(\lambda)$.

Having calculations for $K(\lambda,r)$ and data for $I(\lambda)$ results in an inversion having a number of possible solutions, some of which are not relevant because the inversion is an ill-pose problem. Mathematically, the mathematical inversion may be represented by the matrix of example Equation 13.

$$\begin{bmatrix} I_1 \\ \vdots \\ I_i \\ \vdots \end{bmatrix} = \begin{bmatrix} k_{11} & \cdots & k_{1j} & \cdots \\ \cdots & \cdots & \cdots & \cdots \\ k_{i1} & \cdots & k_{ij} & \cdots \\ \cdots & \cdots & \cdots & \cdots \end{bmatrix} \begin{bmatrix} f_1 \\ \vdots \\ f_j \\ \vdots \end{bmatrix} \Rightarrow \text{Inversion} \begin{bmatrix} f_1 \\ \vdots \\ f_j \\ \vdots \end{bmatrix}. \quad \text{Equation 13}$$

In the form of example Equation 13, if given the matrix multiplication of $K_{ij}*f_j$ picks out resultant ECSC values that give $I=\Sigma K_{ij}f_j$ represented in matrix thou as $I=Kf$. However, when I is given by the data and f represents the unknown densities of each particle size the matrix equation of $I=Kf$ is an overdetermined system of equations, which may be solved for f via a least squares minimization method designed to minimize the sum of squares of the residuals as shown in example Equation 14.

$$\|Kf-I\|^2 \quad \text{Equation 14.}$$

In the illustrated example Equation 14, K may be or singular, which may further result in multiple solutions for f. In the event that one or more solutions of f are oscillatory, no physical meaning is associated with it. To filter out one or more nonphysical solutions, the example inversion engine 218 applies a regularization matrix (block 820). Example. Equation 15 illustrates an example regularization matrix a$\Gamma$ applied to Equation 14 as shown in Equation 15.

$$\|Kf-I\|^2 + \|a\Gamma f\|^2 \quad \text{Equation 15.}$$

The example regularization matrix a$\Gamma$ where a is a regularization parameter may be applied via any method including, but not limited to the Tikhonov Regularization method. Including the regularization factor allows the physical solutions to be revealed while discarding one or more non-meaningful solutions. A Tikhonov matrix $\Gamma$ may include an identity matrix I and regularization parameter a having a value of 1.

Figure 9:
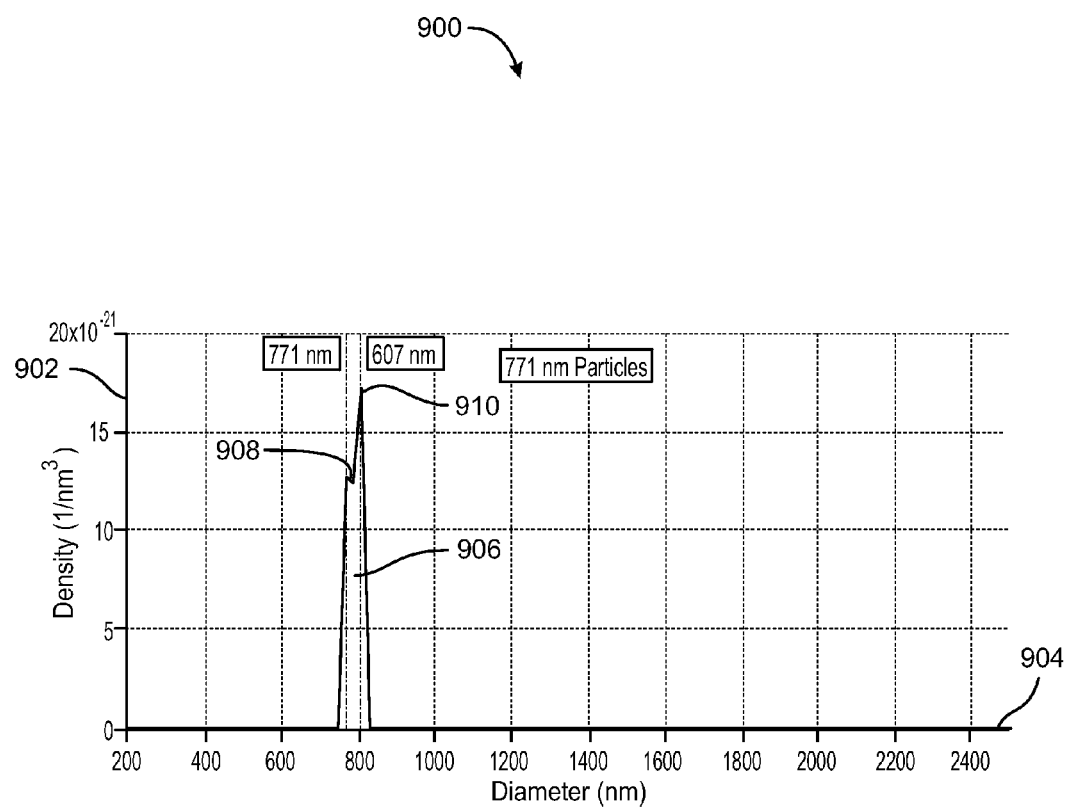
FIG. 9 is an example plot of particle density versus particle diameter for manufacturer sourced polystyrene spheres using transmission-based measurement techniques.

Example output 900 from an inversion and realization process is shown in FIG. 9. In the illustrated example of FIG. 9, a y-axis 902 represents a density of particles present per cubic nanometer, and an x-axis 904 represents a particle diameter (two times the radius). Manufacturer sourced particles were confirmed to be 771 nm diameter spheres with a 5% deviation. The example transmission-based particle measurement system 100 identified a particle distribution 906 having a first peak of 771 nm (908) and a second peak of 807 nm (910), each of which fall within the stated manufacturer tolerance of 5%. The particle size distribution 906 provides particle count information because the y-axis 902 reveals how many particles are present per unit volume at each diameter and all the values in the particle size distribution 906 may be summed. Multiplying the summed density distribution by the volume of the sample reveals a total number of particles in the sample.

Figure 10:
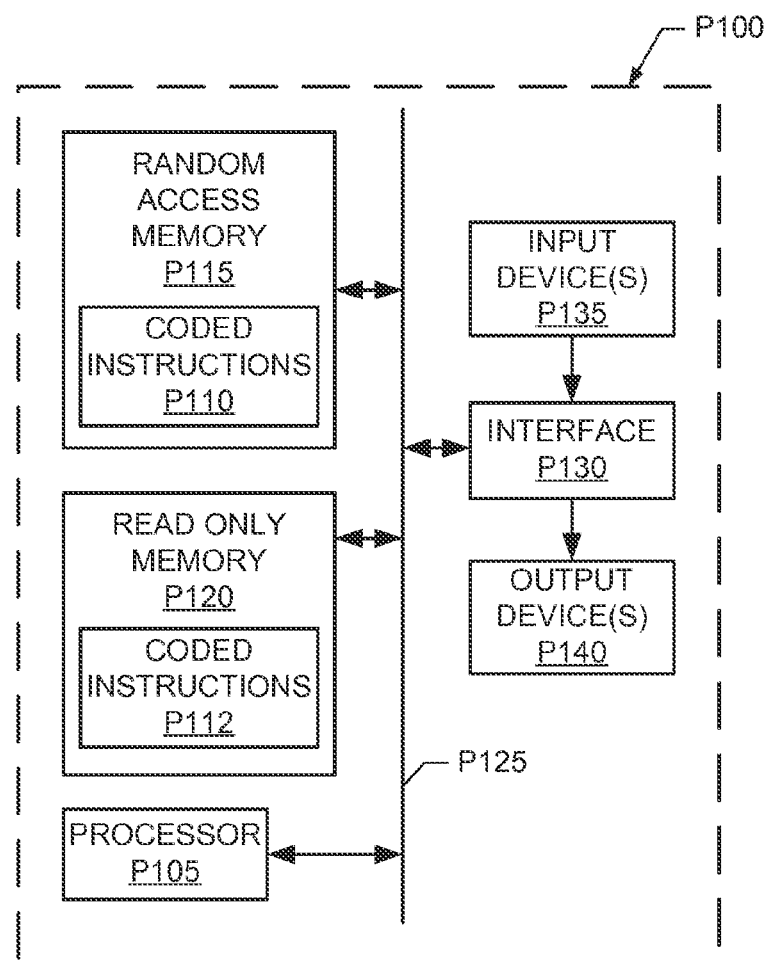
FIG. 10 is a schematic diagram of an example processor platform that may execute the example processes of FIGS. 4-6 and 8 and/or the example transmission measurement controller systems of FIGS. 1A, 1B, 1C and 2.

FIG. 10 is a schematic diagram of an example processor platform P100 that may be used and/or programmed to implement any or all of the example transmission measurement controller 102, the first mirror array 106, the variable wavelength laser 104, the linear slide 110, the motor controlled rotating platform 130, the first photodetector 136a, the second photodetector 136b, the second mirror array 138, the third detector 140a, the fourth detector 140b, the first detector/amplifier 142a, the second detector/amplifier 142b, the light source 152, the rotating sample holder 160, the optical spectrum analyzer 162, the laser controller 202, the sample platform controller 204, the detector interface 206, the calculation engines 208, the profile manager 210, the profile database 212, the experimental extinction coefficient engine 214, the theoretical cross section engine 216 and/or the inversion engine 218 of FIGS. 1A, 1B, 1C and 2. For example, the processor platform P100 can be implemented by one or more general-purpose processors, processor cores, microcontrollers, etc.

The processor platform P100 of the example of FIG. 10 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example processes of FIGS. 4-6 and 8 to implement the example methods and apparatus described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller not shown). The example memory P115 may be used to implement the example profile database 212 of FIG. 2.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130.

Although certain example methods, apparatus and articles of manufacture have been described herein, the scope of coverage of this patent is not limited thereto. On the contrary, this patent covers all methods, apparatus and articles of manufacture fairly failing within the scope of the appended claims either literally or under the doctrine of equivalents.

What is claimed is:

1. An apparatus to identify particle information, comprising:
    A light source capable of emitting light comprising a plurality of wavelengths;
    An optical array to divide emitted light from the light source to a first path and a second path;
    A platform to orient a first and second container with either the first or second path;
    A first and second photodetector to receive at least a direct illuminating component of the emitted light of the first and second path after said light penetrates through the first and second container;
    A detector interface to receive transmission signals from the first and second photodetectors of the direct illuminating component of the emitted light after penetrating through the first and second container; and
    A calculation engine to compute the particle information based on a ratio of the received transmission signals.

2. An apparatus as defined in claim 1, wherein the transmission path of the direct illuminating component is at about a zero angle of exit with respect to an angle of incidence to the first and second container.

3. An apparatus as defined in claim 1, wherein the direct illuminating component of the emitted light of the first and second path received by the first and second photodetector is sensed at one or more wavelengths at the same time.

4. An apparatus as defined in claim 1, wherein the first and second containers are interchanged and the direct illuminating component of the emitted light of the first and second path received by the first and second photodetectors is sensed to balance out errors associated with the received transmission signals.

5. An apparatus as defined in claim 4, wherein the calculation engine calculates ratios of the received transmission signals to determine a transmissivity as a function of wavelength.

6. An apparatus as defined in claim 4, wherein the calculation engine calculates ratios of the received transmission signals to determine an extinction coefficient as a function of wavelength.

7. An apparatus to identify particle information, comprising:
    A light source capable of emitting light comprising a plurality of wavelengths;
    An optical array to divide emitted light from the light source to a first path and a second path;
    A platform to orient a first and second container with either the first or second path;
    A first and second photodetector to receive the emitted light of the first and second path after said light is transmitted through the first and second container;
    A detector interface to receive transmission signals from the first and second photodetectors; and
    A calculation engine to compute the particle information based on a ratio of the received transmission signals
    and further comprising a light source controller to sweep the light source through the plurality of wavelengths and invoke the calculation engine at each of the plurality of wavelengths to calculate an extinction coefficient based on a ratio of the transmission signals to minimize particle information error.

8. An apparatus as defined in claim 1, further comprising a theoretical cross section engine based on Mie theory or Maxwell's equations and applied to the extinction coefficient or transmission signals for each wavelength to extract particle information.

9. An apparatus as defined in claim 1, further comprising an inversion engine to extract a physical solution from an output of the applied Mie theory or Maxwell's equations and to discard nonphysical solutions.

10. An apparatus as defined in claim 1, wherein the first and the second photodetectors are wavelength dependent.

11. An apparatus as defined in claim 1, wherein the first and second photodetectors comprise at least one of a spectrum analyzer or an optical spectrometer.

12. An apparatus of claim 1, wherein the detector interface measures the first and second transmitted paths as a light power as a function of wavelength.

13. An apparatus to measure particles in a suspension, comprising:
    A light source capable of emitting light comprising a plurality of wavelengths;
    A light path having at least a direct illuminating component extending from the light source, through a container, and terminating at a photodetector;
    A platform to alternately orient a first and second container with the light path;
    A detector interface to receive transmission signals from the photodetectors indicative of the direct illuminating component after penetrating through the container; and
    A calculation engine to compute the particle information based on a ratio of the received transmission signals to determine transmissivity as a function of wavelength.

14. An apparatus as defined in claim 13, wherein the light path is at about a zero angle of exit with respect to the angle of incidence to the container.

15. An apparatus as defined in claim 13, wherein the first container holds a sample under test and the second container holds a suspension fluid.

16. An apparatus as defined in claim 13, wherein the photodetector senses the transmitted light at a plurality of wavelengths.

17. An apparatus to measure particles in a suspension, comprising:
    A light source capable of emitting light comprising a plurality of wavelengths;
    A light path extending from the light source, through a container, and terminating at a photodetector configured to sense transmitted light at a plurality of wavelengths;
    A platform to alternately orient a first and second container with the light path;
    A detector interface to receive transmission signals from the photodetectors;
    A calculation engine to compute the particle information based on a ratio of the received transmission signals to determine transmissivity as a function of wavelength, and
    further comprising an experimental extinction coefficient engine invoked at each of the plurality of wavelengths to calculate an extinction coefficient and a theoretical cross section engine based on Mie theory or Maxwell's equations and applied to the ratio of transmission signals for each wavelength to extract particle information.

18. An apparatus as defined in claim 17, further comprising an inversion engine to extract a physical solution from an output of the applied Mie theory or Maxwell's equations and to discard nonphysical solutions.

* * * * *